United States Patent
Ali et al.

(10) Patent No.: US 6,584,336 B1
(45) Date of Patent: Jun. 24, 2003

(54) UNIVERSAL/UPGRADING PULSE OXIMETER

(75) Inventors: Ammar Al Ali, Tustin, CA (US); Don Crothers, Mission Viejo, CA (US); David Dalke, Irvine, CA (US); Mohamed K. Diab, Mission Viejo, CA (US); Julian Goldman, Irvine, CA (US); Massi E. Kiani, Laguna Niguel, CA (US); Michael Lee, Aliso Viejo, CA (US); Jerome Novak, Aliso Viejo, CA (US); Robert Smith, Lake Forest, CA (US); Val E. Vaden, Hillsborough, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 09/516,110

(22) Filed: Mar. 1, 2000

Related U.S. Application Data

(63) Continuation of application No. 09/491,175, filed on Jan. 25, 2000.
(60) Provisional application No. 60/117,097, filed on Jan. 25, 1999, and provisional application No. 60/161,565, filed on Oct. 26, 1999.

(51) Int. Cl.[7] .............................................. A61B 5/00
(52) U.S. Cl. ......................................................... 600/323
(58) Field of Search ................................. 600/300, 323; 128/903, 904

(56) References Cited

U.S. PATENT DOCUMENTS 5,687,717 A    11/1997   Halpern et al.
5,931,791 A     8/1999   Saltzstein et al.

FOREIGN PATENT DOCUMENTS

| EP | 0 601 589 | 9/1993 |
| WO | WO 97/22293 | 6/1997 |
| WO | WO 00/42911 | 7/2000 |

OTHER PUBLICATIONS

Mallinckrodt Product Catalog, Jan. 8, 2000.

Primary Examiner—Eric F. Winakur
(74) Attorney, Agent, or Firm—Knobbe, Martens, Olson & Bear, LLP.

(57) ABSTRACT

A Universal/Upgrading Pulse Oximeter (UPO) comprises a portable unit and a docking station together providing three-instruments-in-one functionality for measuring oxygen saturation and related physiological parameters. The portable unit functions as a handheld pulse oximeter. The combination of the docked portable and the docking station functions as a standalone, high-performance pulse oximeter. The portable-docking station combination is also connectable to, and universally compatible with, pulse oximeters from various manufacturers through use of a waveform generator. The UPO provides a universal sensor to pulse oximeter interface and a pulse oximetry measurement capability that upgrades the performance of conventional instruments by increasing low perfusion performance and motion artifact immunity, for example. Universal compatibility combined with portability allows the UPO to be transported along with patients transferred between an ambulance and a hospital ER, or between various hospital sites, providing continuous patient monitoring in addition to plug-compatibility and functional upgrading for multiparameter patient monitoring systems.

The image on the portable display is rotatable, either manually when undocked or as a function of orientation. In one embodiment, the docking station has a web server and network interface that allows UPO data to be downloaded and viewed as web pages over a local area network or the Internet.

37 Claims, 16 Drawing Sheets

UNIVERSAL/UPGRADING PULSE OXIMETER

This application is a continuation of prior application Ser. No. 09/491,175 filed Jan. 25, 2000, and claims the benefit of priority under 35 U.S.C. §119(e) from U.S. Provisional Application No. 60/117,097, filed Jan. 25, 1999 and Provisional Application No. 60/161,565 filed Oct. 26, 1999.

BACKGROUND OF THE INVENTION

Oximetry is the measurement of the oxygen level status of blood. Early detection of low blood oxygen level is critical in the medical field, for example in critical care and surgical applications, because an insufficient supply of oxygen can result in brain damage and death in a matter -of minutes. Pulse oximetry is a widely accepted noninvasive procedure for measuring the oxygen saturation level of arterial blood, an indicator of oxygen supply. A pulse oximetry system consists of a sensor applied to a patient, a pulse oximeter, and a patient cable connecting the sensor and the pulse oximeter.

The pulse oximeter may be a standalone device or may be incorporated as a module or built-in portion of a multiparameter patient monitoring system, which also provides measurements such as blood pressure, respiratory rate and EKG. A pulse oximeter typically provides a numerical readout of the patient's oxygen saturation, a numerical readout of pulse rate, and an audible indicator or "beep" that occurs in response to each pulse. In addition, the pulse oximeter may display the patient's plethysmograph, which provides a visual display of the patient's pulse contour and pulse rate.

SUMMARY OF THE INVENTION

FIG. 1 illustrates a prior art pulse oximeter 100 and associated sensor 110. Conventionally, a pulse oximetry sensor 110 has LED emitters 112, typically one at a red wavelength and one at an infrared wavelength, and a photodiode detector 114. The sensor 110 is typically attached to an adult patient's finger or an infant patient's foot. For a finger, the sensor 110 is configured so that the emitters 112 project light through the fingernail and through the blood vessels and capillaries underneath. The LED emitters 112 are activated by drive signals 122 from the pulse oximeter 100. The detector 114 is positioned at the fingertip opposite the fingernail so as to detect the LED emitted light as it emerges from the finger tissues. The photodiode generated signal 124 is relayed by a cable to the pulse oximeter 100.

The pulse oximeter 100 determines oxygen saturation ($SpO_2$) by computing the differential absorption by arterial blood of the two wavelengths emitted by the sensor 110. The pulse oximeter 100 contains a sensor interface 120, an $SpO_2$ processor 130, an instrument manager 140, a display 150, an audible indicator (tone generator) 160 and a keypad 170. The sensor interface 120 provides LED drive current 122 which alternately activates the sensor red and IR LED emitters 112. The sensor interface 120 also has input circuitry for amplification and filtering of the signal 124 generated by the photodiode detector 114, which corresponds to the red and infrared light energy attenuated from transmission through the patient tissue site. The $SpO_2$ processor 130 calculates a ratio of detected red and infrared intensities, and an arterial oxygen saturation value is empirically determined based on that ratio. The instrument manager 140 provides hardware and software interfaces for managing the display 150, audible indicator 160 and keypad 170. The display 150 shows the computed oxygen status, as described above. The audible indicator 160 provides the pulse beep as well as alarms indicating desaturation events. The keypad 170 provides a user interface for such things as alarm thresholds, alarm enablement, and display options.

Computation of $SpO_2$ relies on the differential light absorption of oxygenated hemoglobin, $HbO_2$, and deoxygenated hemoglobin, Hb, to determine their respective concentrations in the arterial blood. Specifically, pulse oximetry measurements are made at red and IR wavelengths chosen such that deoxygenated hemoglobin absorbs more red light than oxygenated hemoglobin, and, conversely, oxygenated hemoglobin absorbs more infrared light than deoxygenated hemoglobin, for example 660 nm (red) and 905 nm (IR).

To distinguish between tissue absorption at the two wavelengths, the red and IR emitters 112 are provided drive current 122 so that only one is emitting light at a given time. For example, the emitters 112 may be cycled on and off alternately, in sequence, with each only active for a quarter cycle and with a quarter cycle separating the active times. This allows for separation of red and infrared signals and removal of ambient light levels by downstream signal processing. Because only a single detector 114 is used, it responds to both the red and infrared emitted light and generates a time-division-multiplexed ("modulated") output signal 124. This modulated signal 124 is coupled to the input of the sensor interface 120.

In addition to the differential absorption of hemoglobin derivatives, pulse oximetry relies on the pulsatile nature of arterial blood to differentiate hemoglobin absorption from absorption of other constituents in the surrounding tissues. Light absorption between systole and diastole varies due to the blood volume change from the inflow and outflow of arterial blood at a peripheral tissue site. This tissue site might also comprise skin, muscle, bone, venous blood, fat, pigment, etc., each of which absorbs light. It is assumed that the background absorption due to these surrounding tissues is invariant and can be ignored. Thus, blood oxygen saturation measurements are based upon a ratio of the time-varying or AC portion of the detected red and infrared signals with respect to the time-invariant or DC portion:

$$RD/IR = (Red_{AC}/Red_{DC})/(IR_{AC}/IR_{DC})$$

The desired $SpO_2$ measurement is then computed from this ratio. The relationship between RD/IR and $SpO_2$ is most accurately determined by statistical regression of experimental measurements obtained from human volunteers and calibrated measurements of oxygen saturation. In a pulse oximeter device, this empirical relationship can be stored as a "calibration curve" in a read-only memory (ROM) look-up table so that $SpO_2$ can be directly read-out of the memory in response to input RD/IR measurements.

Pulse oximetry is the standard-of-care in various hospital and emergency treatment environments. Demand has lead to pulse oximeters and sensors produced by a variety of manufacturers. Unfortunately, there is no standard for either performance by, or compatibility between, pulse oximeters or sensors. As a result, sensors made by one manufacturer are unlikely to work with pulse oximeters made by another manufacturer. Further, while conventional pulse oximeters and sensors are incapable of taking measurements on patients with poor peripheral circulation and are partially or fully disabled by motion artifact, advanced pulse oximeters and sensors manufactured by the assignee of the present invention are functional under these conditions. This presents a dilemma to hospitals and other caregivers wishing to upgrade their patient oxygenation monitoring capabilities. They are faced with either replacing all of their conventional pulse oximeters, including multiparameter patient monitoring systems, or working with potentially incompatible sensors and inferior pulse oximeters manufactured by various vendors for the pulse oximetry equipment in use oat the installation.

Hospitals and other caregivers are also plagued by the difficulty of monitoring patients as they are transported from one setting to another. For example, a patient transported by ambulance to a hospital emergency room will likely be unmonitored during the transition from ambulance to the ER and require the removal and replacement of incompatible sensors in the ER. A similar problem is faced within a hospital as a patient is moved between surgery, ICU and recovery settings. Incompatibility and transport problems are exacerbated by the prevalence of expensive and non-portable multiparameter patient monitoring systems having pulse oximetry modules as one measurement parameter.

The Universal/Upgrading Pulse Oximeter (UPO) according to the present invention is focused on solving these performance, incompatibility and transport problems. The UPO provides a transportable pulse oximeter that can stay with and continuously monitor the patient as they are transported from setting to setting. Further, the UPO provides a synthesized output that drives the sensor input of other pulse oximeters. This allows the UPO to function as a universal interface that matches incompatible sensors with other pulse oximeter instruments. Further, the UPO acts as an upgrade to existing pulse oximeters that are adversely affected by low tissue perfusion and motion artifact. Likewise, the UPO can drive a $SpO_2$ sensor input of multiparameter patient monitoring systems, allowing the UPO to integrate into the associated multiparameter displays, patient record keeping systems and alarm management functions.

One aspect of the present invention is a measurement apparatus comprising a sensor, a first pulse oximeter and a waveform generator. The sensor has at least one emitter and an associated detector configured to attach to a tissue site. The detector provides an intensity signal responsive to the oxygen content of arterial blood at the tissue site. The first pulse oximeter is in communication with the detector and computes an oxygen saturation measurement based on the intensity signal. The waveform generator is in communication with the first pulse oximeter and provides a waveform based on the oxygen saturation measurement. A second pulse oximeter is in communication with the waveform generator and displays an oxygen saturation value based on the waveform. The waveform is synthesized so that the oxygen saturation value is generally equivalent to the oxygen saturation measurement.

In another aspect of the present invention, a measurement apparatus comprises a first sensor port connectable to a sensor, an upgrade port, a signal processor and a waveform generator. The upgrade port is connectable to a second sensor port of a physiological monitoring apparatus. The signal processor is configured to compute a physiological measurement based on a signal input to the first sensor port. The waveform generator produces a waveform based on the physiological measurement, and the waveform is available at the upgrade port. The waveform is adjustable so that the physiological monitoring apparatus displays a value generally equivalent to the physiological measurement when the upgrade port is attached to the second sensor port.

Yet another aspect of the present invention is a measurement method comprising the steps of sensing an intensity signal responsive to the oxygen content of arterial blood at a tissue site and computing an oxygen saturation measurement based on the intensity signal. Other steps are generating a waveform based on the oxygen saturation measurement and providing the waveform to the sensor inputs of a pulse oximeter so that the pulse oximeter displays an oxygen saturation value generally equivalent to the oxygen saturation measurement.

An additional aspect of the present invention is a measurement method comprising the steps of sensing a physiological signal, computing a physiological measurement based upon the signal, and synthesizing a waveform as a function of the physiological measurement. A further step is outputting the waveform to a sensor input of a physiological monitoring apparatus. The synthesizing step is performed so that the measurement apparatus displays a value corresponding to the physiological measurement.

A further aspect of the present invention is a measurement apparatus comprising a first pulse oximeter for making an oxygen saturation measurement and a pulse rate measurement based upon an intensity signal derived from a tissue site. Also included is a waveform generation means for creating a signal based upon the oxygen saturation measurement and the pulse rate measurement. In addition, there is a communication means for transmitting the signal to a second pulse oximeter.

Another aspect of the present invention is a measurement apparatus comprising a portable portion having a sensor port, a processor, a display, and a docking connector. The sensor port is configured to receive an intensity signal responsive to the oxygen content of arterial blood at a tissue site. The processor is programmed to compute an oxygen saturation value based upon the intensity signal and to output the value to the display. A docking station has a portable connector and is configured to accommodate the portable so that the docking connector mates with the portable connector. This provides electrical connectivity between the docking station and the portable. The portable has an undocked position separate from the docking station in which the portable functions as a handheld pulse oximeter. The portable also has a docked position at least partially retained within the docking station in which the combination of the portable and the docking station has at least one additional function compared with the portable in the undocked position.

A further aspect of the present invention is a measurement apparatus configured to function in both a first spatial orientation and a second spatial orientation. The apparatus comprises a sensor port configured to receive a signal responsive to a physiological state. The apparatus also has a tilt sensor providing an output responsive to gravity. In addition, there is a processor in communication with the sensor port and the tilt sensor output. The processor is programmed to compute a physiological measurement value based upon the signal and to determine whether the measurement apparatus is in the first orientation or the second orientation based upon the tilt sensor output. A display has a first mode and a second mode and is driven by the processor. The display shows the measurement value in the first mode when the apparatus is in the first orientation and shows the measurement value in the second mode when the apparatus is in the second orientation.

Another aspect of the present invention is a measurement method comprising the steps of sensing a signal responsive to a physiological state and computing physiological measurement based on the signal. Additional steps are determining the spatial orientation of a tilt sensor and displaying the physiological measurement in a mode that is based upon the determining step.

DETAILED DESCRIPTION OF THE PREFERRED EMBODIMENTS

Figure 1:
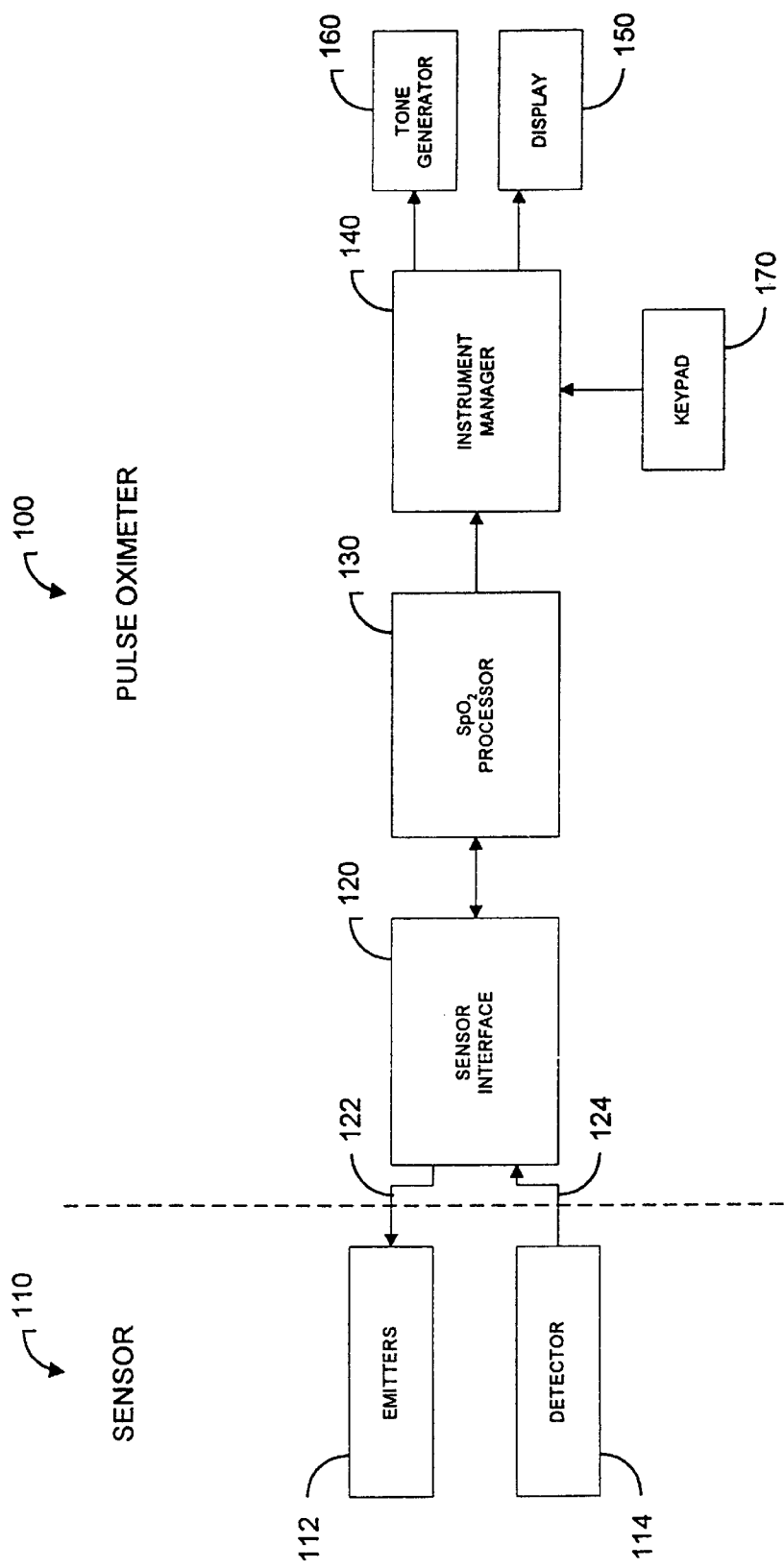
FIG. 1 is a block diagram of a prior art pulse oximeter.
Figure 2:
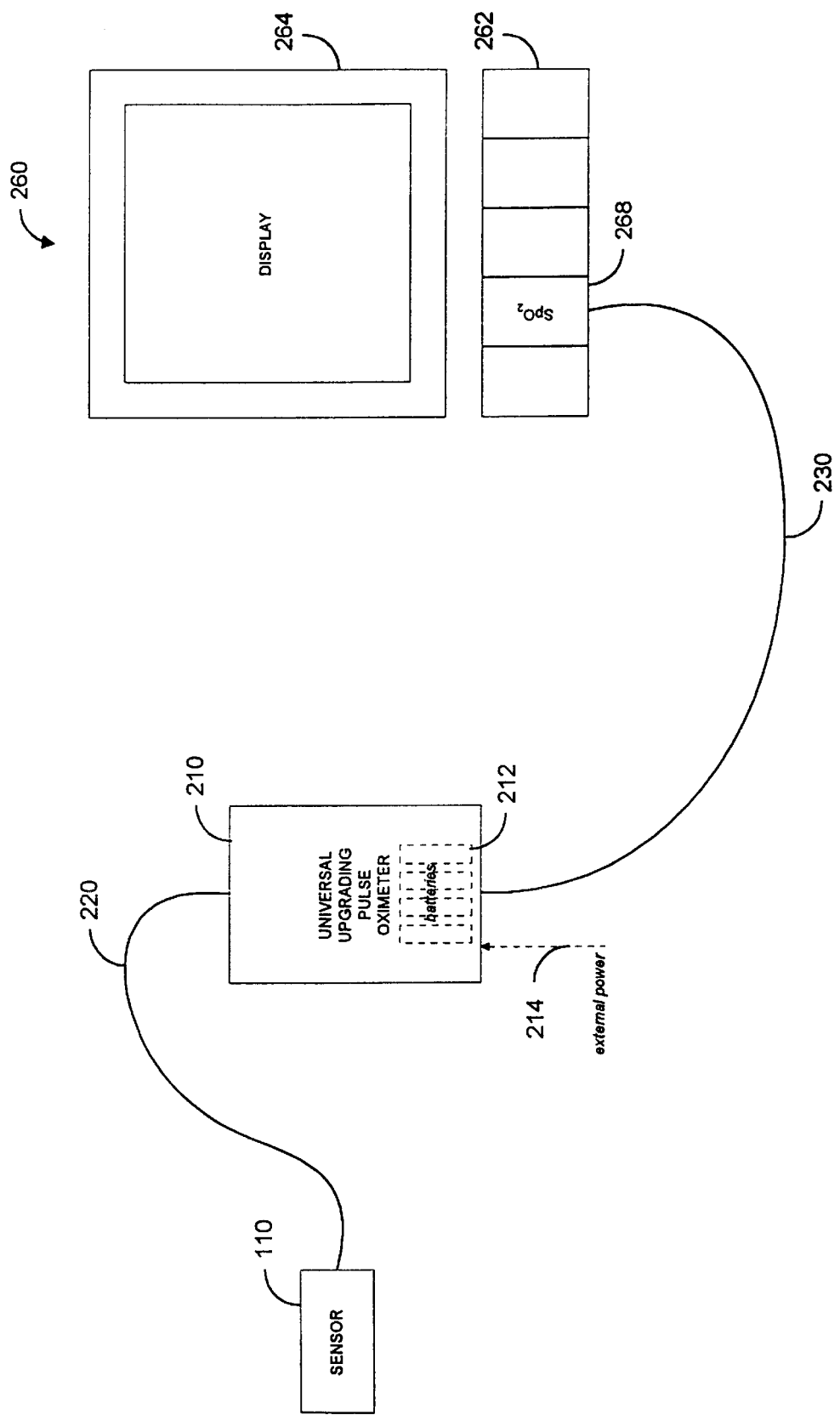
FIG. 2 is a diagram illustrating a patient monitoring system incorporating a universal/upgrading pulse oximeter (UPO) according to the present invention.

FIG. 2 depicts the use of a Universal/Upgrading Pulse Oximeter ("UPO") 210 to perform patient monitoring. A pulse oximetry sensor 110 is attached to a patient (not illustrated) and provides the UPO 210 with a modulated red and IR photo-plethysmograph signal through a patient cable 220. The UPO 210 computes the patient's oxygen saturation and pulse rate from the sensor signal and, optionally, displays the patient's oxygen status. The UPO 210 may incorporate an internal power source 212, such as common alkaline batteries or a rechargeable power source. The UPO 210 may also utilize an external power source 214, such as standard 110V AC coupled with an external step-down transformer and an internal or external AC-to-DC converter.

In addition to providing pulse oximetry measurements, the UPO 210 also separately generates a signal, which is received by a pulse oximeter 268 external to the UPO 210. This signal is synthesized from the saturation calculated by the UPO 210 such that the external pulse oximeter 268 calculates the equivalent saturation and pulse rate as computed by the UPO 210. The external pulse oximeter 268 receiving the UPO signal may be a multiparameter patient monitoring system (MPMS) 260 incorporating a pulse oximeter module 268, a standalone pulse oximeter instrument, or any other host instrument capable of measuring $SpO_2$. The MPMS 260 depicted in FIG. 2 has a rack 262 containing a number of modules for monitoring such patient parameters as blood pressure, EKG, respiratory gas, and $SpO_2$. The measurements made by these various modules are shown on a multiparameter display 264, which is typically a video (CRT) device. The UPO 210 is connected to an existing MPMS 260 with a cable 230, advantageously integrating the UPO oxygen status measurements with other MPMS measurements. This allows the UPO calculations to be shown on a unified display of important patient parameters, networked with other patient data, archived within electronic patient records and incorporated into alarm management, which are all MPMS functions convenient to the caregiver.

Figure 3:
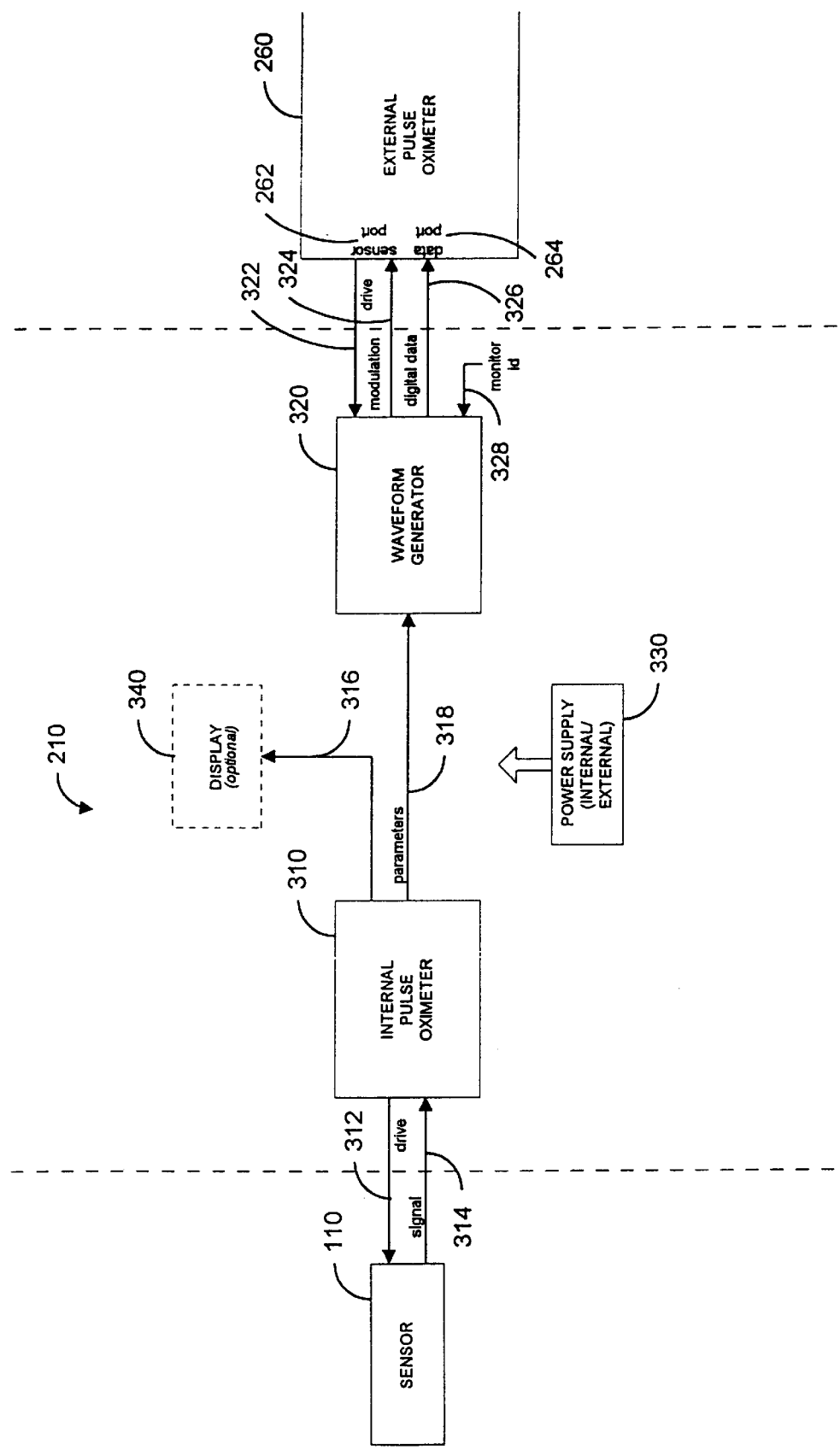
FIG. 3 is top level block diagram of a UPO embodiment.

FIG. 3 depicts the major functions of the UPO 210, including an internal pulse oximeter 310, a waveform generator 320, a power supply 330 and an optional display 340. Attached to the UPO 210 is a sensor 110 and an external pulse oximeter 260. The internal pulse oximeter 310 provides the sensor 110 with a drive signal 312 that alternately activates the sensor's red and IR LEDs, as is well-known in the art. A corresponding detector signal 314 is received by the internal pulse oximeter 310. The internal pulse oximeter 310 computes oxygen saturation, pulse rate, and, in some embodiments, other physiological parameters such as pulse occurrence, plethysmograph features and measurement confidence. These parameters 318 are output to the waveform generator 320. A portion of these parameters may also be used to generate display drive signals 316 so that patient status may be read from, for example, an LED or LCD display module 340 on the UPO.

The internal pulse oximeter 310 may be a conventional pulse oximeter or, for upgrading an external pulse oximeter 260, it may be an advanced pulse oximeter capable of low perfusion and motion artifact performance not found in conventional pulse oximeters. An advanced pulse oximeter for use as an internal pulse oximeter 310 is described in U.S. Pat. No. 5,632,272 assigned to the assignee of the present invention and incorporated herein by reference. An advanced pulse oximetry sensor for use as the sensor 110 attached to the internal pulse oximeter 310 is described in U.S. Pat. No. 5,638,818 assigned to the assignee of the present invention and incorporated herein by reference. Further, a line of advanced Masimo SET® pulse oximeter OEM boards and sensors are available from the assignee-of the present invention.

The waveform generator 320 synthesizes a waveform, such as a triangular waveform having a sawtooth or symmetric triangle shape, that is output as a modulated signal 324 in response to an input drive signal 322. The drive input 322 and modulation output 324 of the waveform generator 320 are connected to the sensor port 262 of the external pulse oximeter 260. The synthesized waveform is generated in a manner such that the external pulse oximeter 260 computes and displays a saturation and a pulse rate value that is equivalent to that measured by the internal pulse oximeter 310 and sensor 110. In the present embodiment, the waveforms for pulse oximetry are chosen to indicate to the external pulse oximeter 260 a perfusion level of 5%. The external pulse oximeter 260, therefore, always receives a strong signal. In an alternative embodiment, the perfusion level of the waveforms synthesized for the external pulse oximeter can be set to indicate a perfusion level at or close to the perfusion level of the patient being monitored by the internal pulse oximeter 310. As an alternative to the generated wavefor, a digital data output 326, is connected to the data port 264 of the external pulse oximeter 260. In this manner, saturation and pulse rate measurements and also samples of the unmodulated, synthesized waveform can be communicated directly to the external pulse oximeter 260 for display, bypassing the external pulse oximeter's signal processing functions. The measured plethysmograph waveform samples output from the internal pulse oximeter 310 also may be communicated through the digital data output 326 to the external pulse oximeter 260.

It will be understood from the above discussion that the synthesized waveform is not physiological data from the patient being monitored by the internal pulse oximeter 310, but is a waveform synthesized from predetermined stored waveform data to cause the external pulse oximeter 260 to calculate oxygen saturation and pulse rate equivalent to or generally equivalent (within clinical significance) to that calculated by the internal pulse oximeter 310. The actual physiological waveform from the patient received by the detector is not provided to the external pulse oximeter 260 in the present embodiment. Indeed, the waveform provided to the external pulse oximeter will usually not resemble the plethysmographic waveform of physiological data from the patient being monitored by the internal pulse oximeter 260.

The cable 230 (FIG. 2) attached between the waveform generator 320 and external pulse oximeter 260 provides a monitor ID 328 to the UPO, allowing identification of predetermined external pulse oximeter calibration curves. For example, this cable may incorporate an encoding device, such as a resistor, or a memory device, such as a PROM 1010 (FIG. 10) that is read by the waveform generator 320. The encoding device provides a value that uniquely identifies a particular type of external pulse oximeter 260 having known calibration curve, LED drive and modulation signal characteristics. Although the calibration curves of the external pulse oximeter 260 are taken into account, the wavelengths of the actual sensor 110, advantageously, are not required to correspond to the particular calibration curve indicated by the monitor ID 328 or otherwise assumed for the external pulse oximeter 260. That is, the wavelength of the sensor 110 attached to the internal pulse oximeter 310 is not relevant or known to the external pulse oximeter 260.

Figure 4:
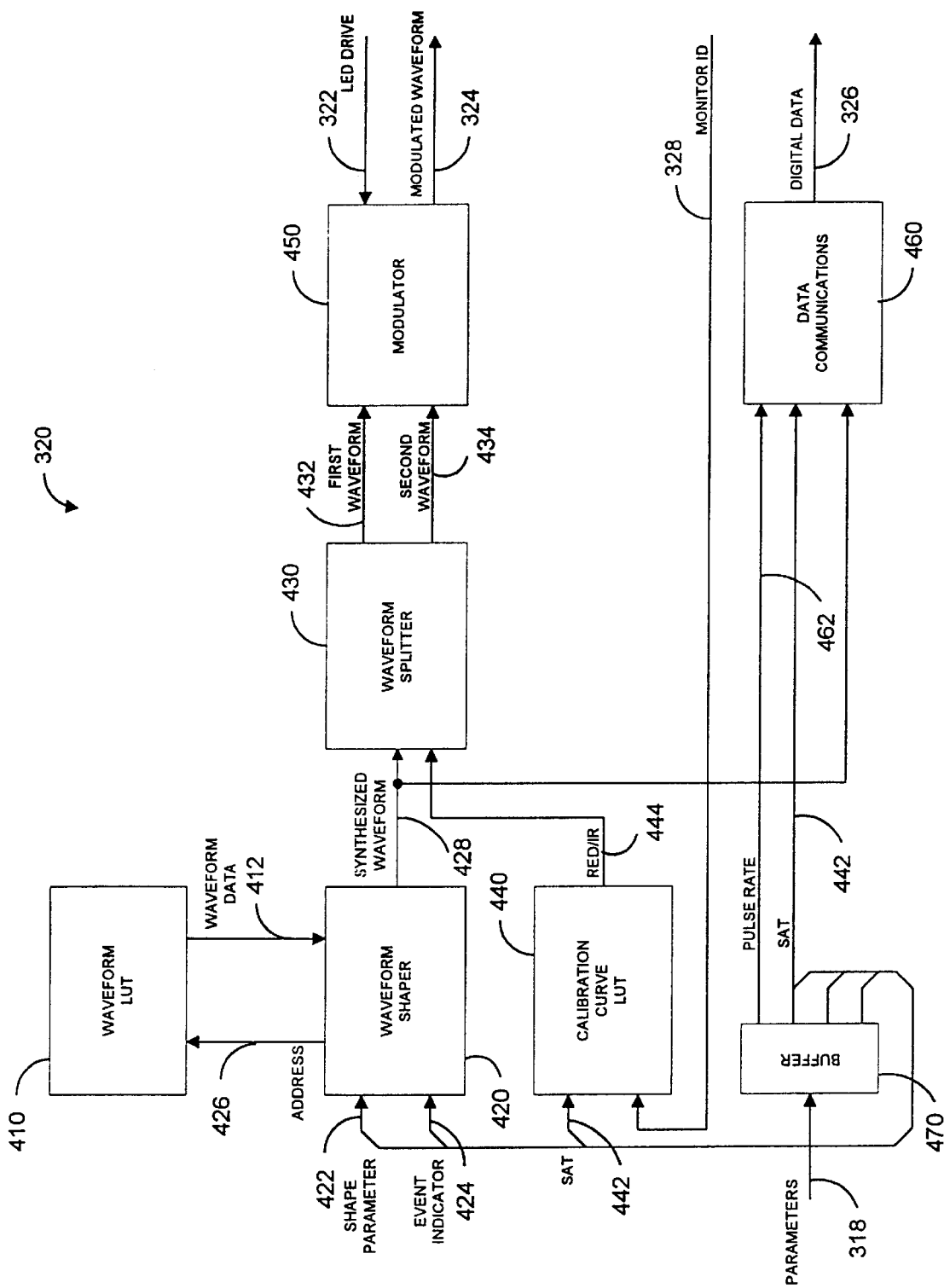
FIG. 4 is a detailed block diagram of the waveform generator portion of the UPO embodiment shown in FIG. 3.

FIG. 4 illustrates one embodiment of the waveform generator portion 320 of the UPO 210 (FIG. 3). Although this embodiment is illustrated and described as hardware, one of ordinary skill will recognize that the functions of the waveform generator may be implemented in software or firmware or a combination of hardware, software and firmware. The waveform generator 320 performs waveform synthesis with a waveform look-up table ("LUT") 410, a waveform shaper 420 and a waveform splitter 430. The waveform LUT 410 is advantageously a memory device, such as a ROM (read only memory) that contains samples of one or more waveform portions or segments containing a single waveform. These stored waveform segments may be as simple as a single period of a triangular waveform, having a sawtooth or symmetric triangle shape, or more complicated, such as a simulated plethysmographic pulse having various physiological features, for example rise time, fall time and dicrotic notch.

The waveform shaper 420 creates a continuous pulsed waveform from the waveform segments provided by the waveform LUT 410. The waveform shaper 420 has a shape parameter input 422 and an event indicator input 424 that are buffered 470 from the parameters 318 output from the internal pulse oximeter 310 (FIG. 3). The shape parameter input 422 determines a particular waveform segment in the waveform LUT 410. The chosen waveform segment is specified by the first address transmitted to the waveform LUT 410 on the address lines 426. The selected waveform segment is sent to the waveform shaper 420 as a series of samples on the waveform data lines 412.

The event indicator input 424 specifies the occurrence of pulses in the plethysmograph waveform processed by the internal pulse oximeter 310 (FIG. 3). For example, the event indicator may be a delta time from the occurrence of a previously detected falling pulse edge or this indicator could be a real time or near real time indicator of the pulse occurrence. The waveform shaper 420 accesses the waveform LUT 410 in a manner to create a corresponding delta time between pulses in the synthesized waveform output 428. In one embodiment, the waveform shaper is clocked at a predetermined sample rate. From a known number of samples per stored waveform segment and the input delta time from the event indicator, the waveform shaper 420 determines the number of sequential addresses to skip between samples and accesses the waveform LUT 410 accordingly. This effectively "stretches" or "shrinks" the retrieved waveform segment so as to fit in the time between two consecutive pulses detected by the UPO.

The waveform splitter 430 creates a first waveform 432 corresponding to a first waveform (such a red wavelength) expected by the external pulse oximeter 260 (FIG. 3) and a second waveform (such as infrared) 434 expected by the external pulse oximeter 260. The relative amplitudes of the first waveform 432 and second waveform 434 are adjusted to correspond to the ratio output 444 from a calibration curve LUT 440. Thus, for every value of measured oxygen saturation at the sat input 442, the calibration curve LUT 440 provides a corresponding ratio output 444 that results in the first waveform 432 and the second waveform 434 having an amplitude ratio that will be computed by the external pulse oximeter 260 (FIG. 3) as equivalent to the oxygen saturation measured by the internal pulse oximeter 310 (FIG. 3).

As described above, one particularly advantageous aspect of the UPO is that the operating wavelengths of the sensor 110 (FIG. 3) are not relevant to the operating wavelengths required by the external pulse oximeter 260 (FIG. 3), i.e. the operating wavelengths that correspond to the calibration curve or curves utilized by the external pulse oximeter. The calibration curve LUT 440 simply permits generation of a synthesized waveform as expected by the external oximeter 260 (FIG. 3) based on the calibration curve used by the external pulse oximeter 260 (FIG. 3). The calibration curve LUT 440 contains data about the known calibration curve of the external pulse oximeter 260 (FIG. 3), as specified by the monitor ID input 328. In other words, the waveform actually synthesized is not a patient plethysmographic waveform. It is merely a stored waveform that will cause the external pulse oximeter to calculate the proper oxygen saturation valve and pulse rate values. Although this does not provide a patient plethysmograph on the external pulse oximeter for the clinician, the calculated values, which is what is actually sought, will be accurate.

A modulator 450 responds to an LED drive input 322 to generate a modulated waveform output 324 derived from the first waveform 432 and second waveform 434. Also, a data communication interface 460 transmits as a digital data output 326 the data obtained from the sat 442, pulse rate 462 and synthesized waveform 428 inputs.

Figure 5:
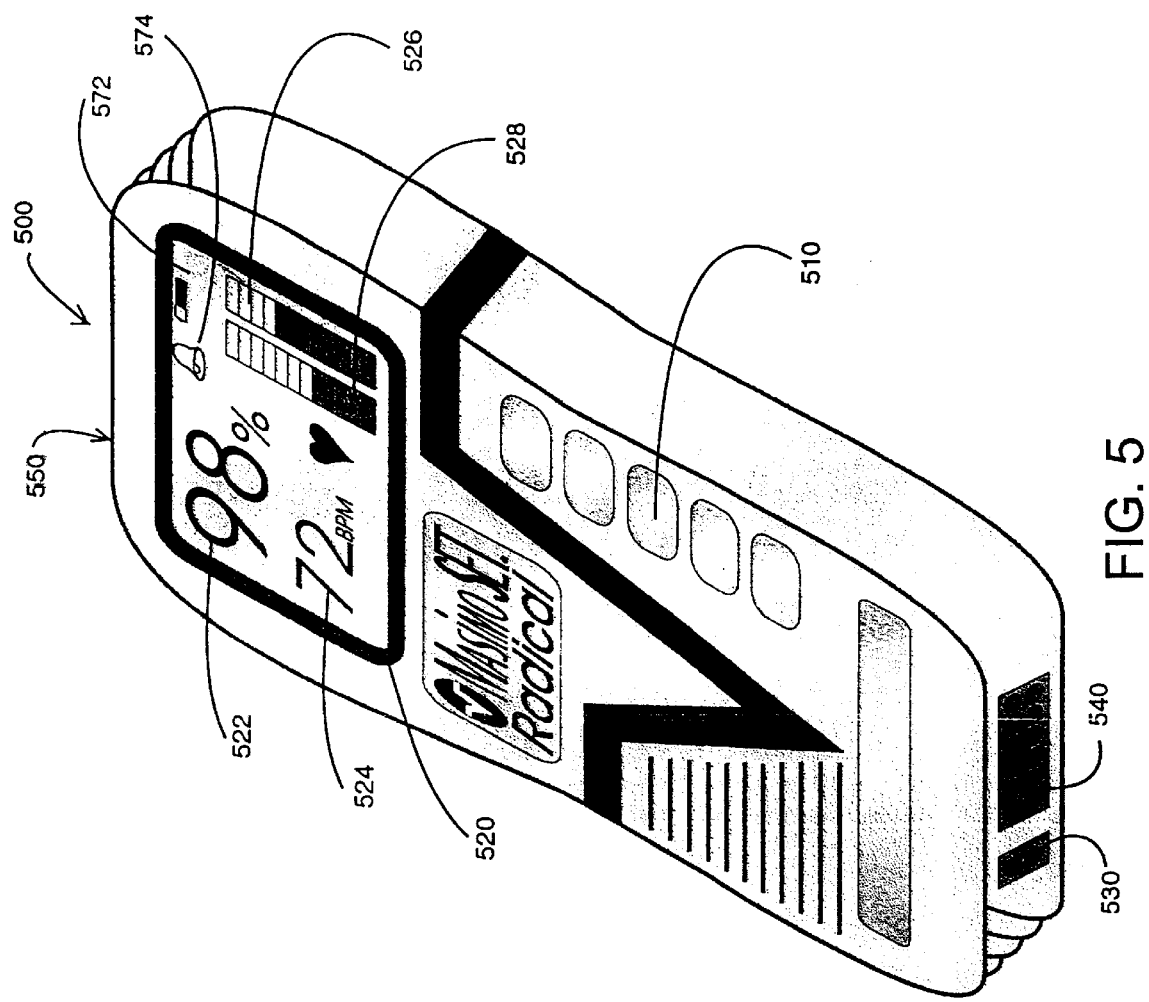
FIG. 5 is an illustration of a handheld embodiment of the UPO.

FIG. 5 depicts a handheld UPO 500 embodiment. The handheld UPO 500 has keypad inputs 510, an LCD display 520, an external power supply input 530, an output port 540 for connection to an external pulse oximeter and a sensor input 550 at the top edge (not visible). The display 520 shows the measured oxygen saturation 522, the measured pulse rate 524, a pulsating bar 526 synchronized with pulse rate or pulse events, and a confidence bar 528 indicating confidence in the measured values of saturation and pulse rate. Also shown are low battery 572 and alarm enabled 574 status indicators.

The handheld embodiment described in connection with FIG. 5 may also advantageously function in conjunction with a docking station that mechanically accepts, and electrically connects to, the handheld unit. The docking station may be co-located with a patient monitoring system and connected to a corresponding $SpO_2$ module sensor port, external power supply, printer and telemetry device, to name a few options. In this configuration, the handheld UPO may be removed from a first docking station at one location to accompany and continuously monitor a patient during transport to a second location. The handheld UPO can then be conveniently placed into a second docking station upon arrival at the second location, where the UPO measurements are displayed on the patient monitoring system at that location.

Figure 6:
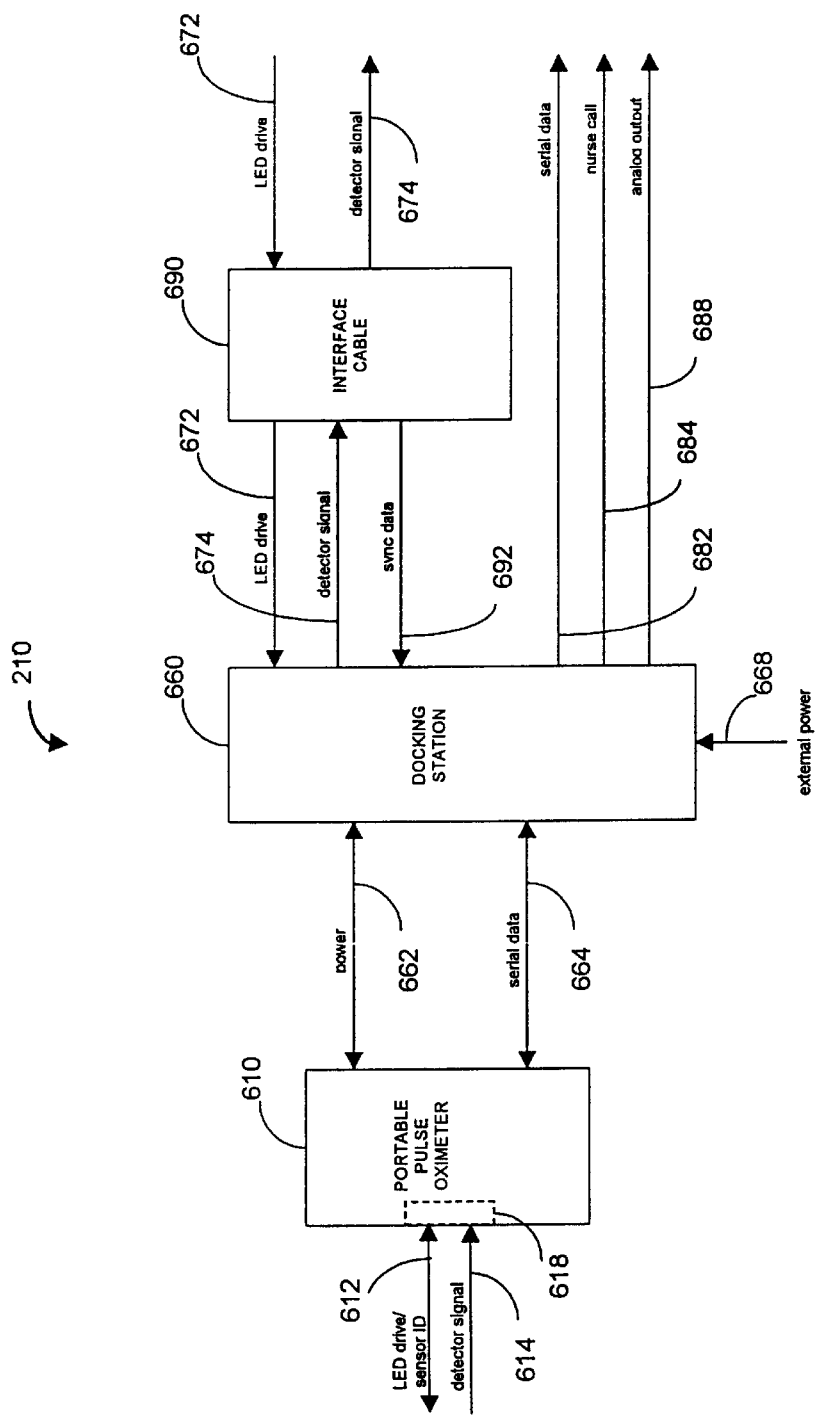
FIG. 6 is a top level block diagram of another UPO embodiment incorporating a portable pulse oximeter and a docking station.

FIG. 6 shows a block diagram of a UPO embodiment, where the functions of the UPO 210 are split between a portable pulse oximeter 610 and a docking station 660. The portable pulse oximeter 610 ("portable") is a battery operated, fully functional, stand-alone pulse oximeter instrument. The portable 610 connects to a sensor 110 (FIG. 2) through a UPO patient cable 220 (FIG. 2) attached to a patient cable connector 618. The portable 610 provides the sensor 110 with a drive signal 612 that alternately activates the sensor's red and IR LEDs, as is well-known in the art. The portable also receives a corresponding detector signal 614 from the sensor. The portable can also input a sensor ID on the drive signal line 612, as described in U.S. Pat. No. 5,758,644 entitled Manual and Automatic Probe Calibration, assigned to the assignee of the present invention and incorporated herein by reference.

The portable 610 can be installed into the docking station 660 to expand its functionality. When installed, the portable 610 can receive power 662 from the docking station 660 if the docking station 660 is connected to external power 668. Alternately, with no external power 668 to the docking, station 660, the portable 610 can supply power 662 to the docking station 660. The portable 610 communicates to the docking station with a bi-directional serial data line 664. In particular, the portable 610 provides the docking station with $SpO_2$, pulse rate and related parameters computed from the sensor detector signal 614. When the portable 610 is installed, the docking station 660 may drive a host instrument 260 (FIG. 2) external to the portable 610. Alternatively, the portable 610 and docking station 660 combination may function as a standalone pulse oximeter instrument, as described below with respect to FIG. 13.

In one embodiment, the docking station 660 does not perform any action when the portable 610 is not docked. The user interface for the docking station 660, i.e. keypad and display, is on the portable 610. An indicator LED on the docking station 660 is lit when the portable is docked. The docking station 660 generates a detector signal output 674 to the host instrument 260 (FIG. 2) in response to LED drive signals 672 from the host instrument and $SpO_2$ values and related parameters received from the portable 610. The docking station 660 also provides a serial data output 682, a nurse call 684 and an analog output 688.

An interface cable 690 connects the docking station 660 to the host instrument patient cable 230 (FIG. 2). The LED drive signals 672 and detector signal output 674 are communicated between the docking station 660 and the host instrument 260 (FIG. 2) via the interface cable 690. The interface cable 690 provides a sync data output 692 to the docking station 660, communicating sensor, host instrument (e.g. monitor ID 328, FIG. 3) and calibration curve data. Advantageously, this data allows the docking station 660 to appear to a particular host instrument as a particular sensor providing patient measurements.

Figure 7:
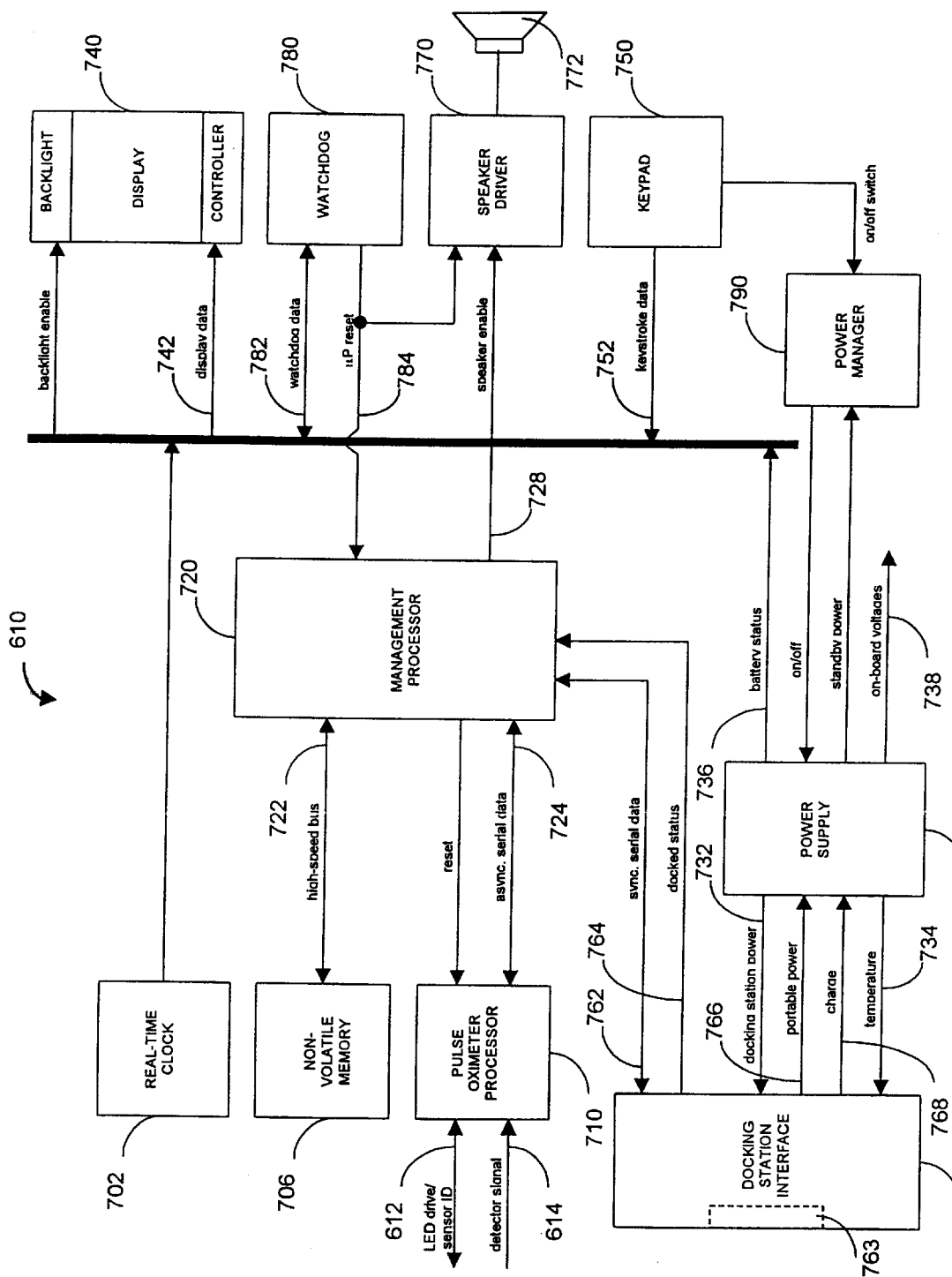
FIG. 7 is a detailed block diagram of the portable pulse oximeter portion of FIG. 6.

FIG. 7 provides further detail of the portable 610. The portable components include a pulse oximeter processor 710, a management processor 720, a power supply 730, a display 740 and a keypad 750. The pulse oximeter processor 710 functions as an internal pulse oximeter, interfacing the portable to a sensor 110 (FIG. 2) and deriving $SpO_2$, pulse rate, a plethysmograph and a pulse indicator. An advanced pulse oximeter for use as the pulse oximeter processor 710 is described in U.S. Pat. No. 5,632,272, referenced above. An advanced pulse oximetry sensor for use as the sensor 110 (FIG. 2) attached to the pulse oximeter processor 710 is described in U.S. Pat. No. 5,638,818, also referenced above. Further, a line of advanced Masimo SET® pulse oximeter OEM boards and sensors are available from the assignee of the present invention. In one embodiment, the pulse oximeter processor 710 is the Masimo SEr® MS-3L board or a low power MS-5 board.

The management processor 720 controls the various functions of the portable 610, including asynchronous serial data communications 724 with the pulse oximeter processor 710 and synchronous serial communications 762 with the docking station 660 (FIG. 6). The physical and electrical connection to the docking station 660 (FIG. 6) is via a docking station connector 763 and the docking station interface 760, respectively. The processor 720 utilizes a real-time clock 702 to keep the current date and time, which includes time and date information that is stored along with $SpO_2$ parameters to create trend data. The processor of the portable 610 and the docking station 660 (FIG. 6) can be from the same family to share common routines and minimize code development time.

The processor 720 also controls the user interface 800 (FIG. 8A) by transferring data 742 to the display 740, including display updates and visual alarms, and by interpreting keystroke data 752 from the keypad 750. The processor 720 generates various alarm signals, when required, via an enable signal 728, which controls a speaker driver 770. The speaker driver 770 actuates a speaker 772, which provides audible indications such as, for example, alarms and pulse beeps. The processor 720 also monitors system status, which includes battery status 736, indicating battery levels, and docked status 764, indicating whether the portable 610 is connected to the docking station 660 (FIG. 6). When the portable 610 is docked and is on, the processor 720 also decides when to turn on or off docking station power 732.

Advantageously, the caregiver can set (i.e. configure or program) the behavior of the portable display 740 and alarms when the docked portable 610 senses that an interface cable 690 has connected the docking station 660 to an external pulse oximeter, such as a multiparameter patient monitoring system. In one user setting, for example, the portable display 740 stops showing the $SpO_2$ 811 (FIG. 8) and pulse rate 813 (FIG. 8) values when connected to an external pulse oximeter to avoid confusing the caregiver, who can read equivalent values on the patient monitoring system. The display 740, however, continues to show the plethysmograph 815 (FIG. 8) and visual pulse indicator 817

(FIG. 8) waveforms. For one such user setting, the portable alarms remain active.

Another task of the processor 720 includes maintenance of a watchdog function. The watchdog 780 monitors processor status on the watchdog data input 782 and asserts the UP reset output 784 if a fault is detected. This resets the management processor 720, and the fault is indicated with audible and visual alarms.

The portable 610 gets its power from batteries in the power supply 730 or from power 766 supplied from the docking station 660 (FIG. 6) via the docking station interface 760. A power manager 790 monitors the on/off switch on the keypad 750 and turns-on the portable power accordingly. The power manager 790 turns off the portable on command by the processor 720. DC/DC converters within the power supply 730 generate the required voltages 738 for operation of the portable 610 and docking station power 732. The portable batteries can be either alkaline rechargeable batteries or another renewable power source. The batteries of the power supply 730 supply docking station power 732 when the docking station 660 (FIG. 6) is without external power. A battery charger within the docking station power supply provides charging current 768 to rechargeable batteries within the power supply 730. The docking station power supply 990 (FIG. 9) monitors temperature 734 from a thermistor in the rechargeable battery pack, providing an indication of battery charge status.

A non-volatile memory 706 is connected to the management processor 720 via a high-speed bus 722. In the present embodiment, the memory 706 is an erasable and field re-programmable device used to store boot data, manufacturing serial numbers, diagnostic failure history, adult $SpO_2$ and pulse rate alarm limits, neonate $SpO_2$ and pulse rate alarm limits, $SpO_2$ and pulse rate trend data, and program data. Other types of non-volatile memory are well known. The $SpO_2$ and pulse rate alarm limits, as well as $SpO_2$ related algorithm parameters, may be automatically selected based on the type of sensor 110 (FIG. 2), adult or neonate, connected to the portable 610.

The LCD display 740 employs LEDs for a backlight to increase its contrast ratio and viewing distance when in a dark environment. The intensity of the backlight is determined by the power source for the portable 610. When the portable 610 is powered by either a battery pack within its power supply 730 or a battery pack in the docking station power supply 990 (FIG. 9), the backlight intensity is at a minimum level. When the portable 610 is powered by external power 668 (FIG. 6), the backlight is at a higher intensity to increase viewing distance and angle. In one embodiment, button on the portable permits overriding these intensity settings, and provides. adjustment of the intensity. The backlight is controlled in two ways. Whenever any key is pressed, the backlight is illuminated for a fixed number of seconds and then turns off, except when the portable is docked and derives power from an external source. In that case, the backlight is normally on unless deactivated with a key on the portable 610.

Figures 8A, 8B, 8C:
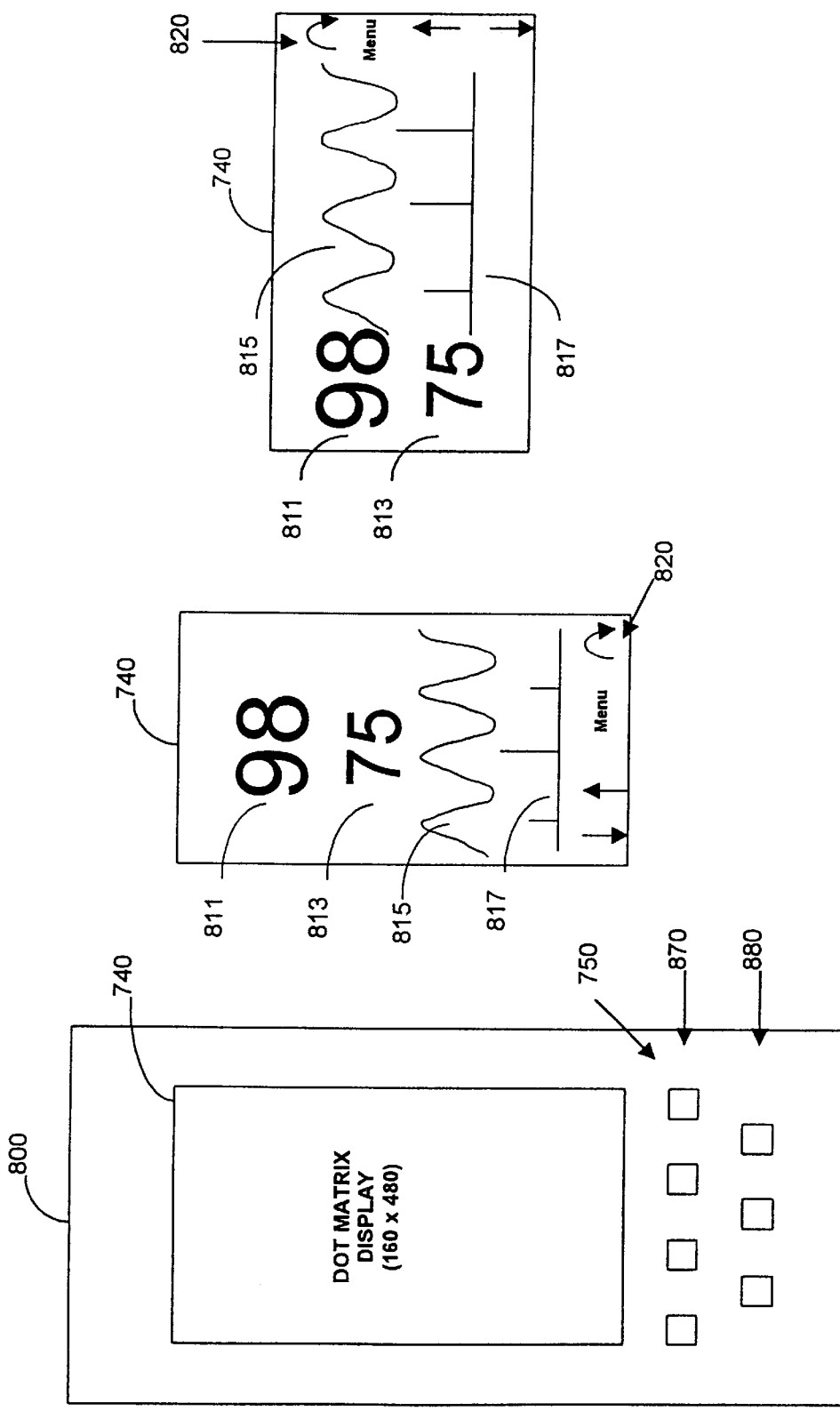
FIG. 8A is an illustration of the portable pulse oximeter user interface, including a keyboard and display.
FIGS. 8B–C are illustrations of the portable pulse oximeter display showing portrait and landscape modes, respectively.

FIG. 8A illustrates the portable user interface 800, which includes a display 740 and a keypad 750. In one embodiment, the display 740 is a dot matrix LCD device having 160 pixels by 480 pixels. The display 740 can be shown in portrait mode, illustrated in FIG. 8B, or in landscape mode, illustrated in FIG. 8C. A tilt sensor 950 (FIG. 9) in the docking station 660 (FIG. 6) or a display mode key on the portable 610 (FIG. 6) determines portrait or landscape mode. The tilt sensor 950 (FIG. 9) can be a gravity-activated switch or other device responsive to orientation and can be alternatively located in the portable 610 (FIG. 6). In a particular embodiment, the tilt sensor 950 (FIG. 9) is a non-mercury tilt switch, part number CW 1300-1, available from Comus International, Nutley, N.J. (www.comus-intl.com). The tilt sensor 950 (FIG. 9) could also be a mercury tilt switch.

Examples of how the display area can be used to display $SpO_2$ 811, pulse rate 813, a plethysmographic waveform 815, a visual pulse indicator 817 and soft key icons 820 in portrait and landscape mode are shown in FIGS. 8B and 8C, respectively. The software program of the management processor 720 (FIG. 7) can be easily changed to modify the category, layout and size of the display information shown in FIGS. 8B–C. Other advantageous information for display is $SpO_2$ limits, alarm, alarm disabled, exception messages and battery status.

The keypad 750 includes soft keys 870 and fixed keys 880. The fixed keys 880 each have a fixed function. The 'soft keys 870 each have a function that is programmable and indicated by one of the soft key icons 820 located next to the soft keys 870. That is, a particular one of the soft key icons 820 is in proximity to a particular one of the soft keys 870 and has a text or a shape that suggests the function of that particular one of the soft keys 870. In one embodiment, the button portion of each key of the keypad 750 is constructed of florescent material so that the keys 870, 880 are readily visible in the dark.

In one embodiment, the keypad 750 has one row of four soft keys 870 and one row of three fixed keys 880. Other configurations are, of course, available, and specific arrangement is not significant. The functions of the three fixed keys 880 are power, alarm silence and light/contrast. The power function is an on/off toggle button. The alarm silence function and the light/contrast function have dual purposes depending on the duration of the key press. A momentary press of the key corresponding to the alarm silence function will disable the audible alarm for a fixed period of time. To disable the audible alarm indefinitely, the key corresponding to the alarm silence function is held down for a specified length of time. If the key corresponding to the alarm silence function is pressed while the audible alarm has been silenced, the audible alarm is reactivated. If the key corresponding to the light/contrast function is pressed momentarily, it is an on/off toggle button for the backlight. If the key corresponding to the light/contrast function is held down, the display contrast cycles through its possible values.

In this embodiment, the default functions of the four soft keys 870 are pulse beep up volume, pulse beep down volume, menu select, and display mode. These functions are indicated on the display by the up arrow, down arrow, "menu" and curved arrow soft key icons 820, respectively. The up volume and down volume functions increase or decrease the audible sound or "beep" associated with each detected pulse. The display mode function rotates the display 740 through all four orthogonal orientations, including portrait mode (FIG. 8B) and landscape mode (FIG. 8C), with each press of the corresponding key. The menu select function allows the functionality of the soft keys 870 to change from the default functions described above. Examples of additional soft key functions that can be selected using this menu feature are set $SpO_2$ high/low limit, set pulse rate high/low limit, set alarm volume levels, set display to show trend data, print trend data, erase trend data, set averaging time, set sensitivity mode, perform synchronization, perform rechargeable battery maintenance (deep discharge/recharge to remove battery memory), and display product version number.

Figure 9:
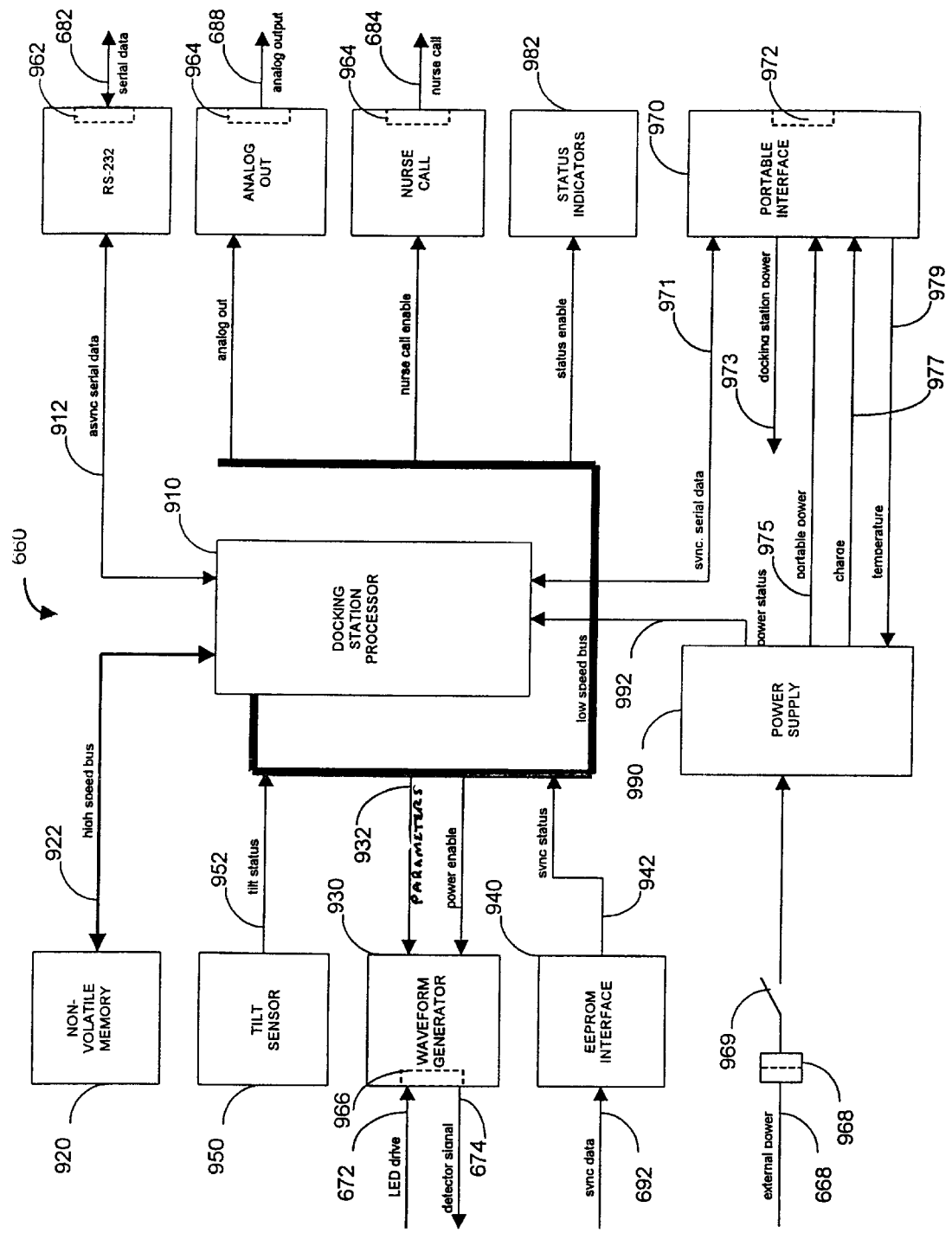
FIG. 9 is a detailed block diagram of the docking station portion of FIG. 6.

FIG. 9 provides further details of the docking station 660, which includes a docking station processor 910, a non-volatile memory 920, a waveform generator 930, a PROM interface 940, a tilt sensor 950, a portable interface 970 and associated connector 972, status indicators 982, a serial data port 682, a nurse call output 684, an analog output 688 and a power supply 990. In one embodiment, the docking station 660 is intended to be associated with a fixed (non-transportable) host instrument, such as a multiparameter patient monitoring instrument in a hospital emergency room. In a transportable embodiment, the docking station 660 is movable, and includes a battery pack within the power supply 990.

The docking station processor 910 orchestrates the activity on the docking station 660. The processor 910 provides the waveform generator 930 with parameters 932 as discussed above for FIGS. 3 and 4. The processor 910 also provides asynchronous serial data 912 for communications with external devices and synchronous serial data 971 for communications with the portable 610 (FIG. 6) in addition, the processor 910 determines system status including sync status 942, tilt status 952 and power status 992. The portable management processor 720 (FIG. 7) performs the watchdog function for the docking station processor 910. The docking station processor 910 sends watchdog messages to the portable processor 720 (FIG. 7) as part of the synchronous serial data 972 to ensure the correct operation of the docking station processor 910.

The docking station processor 910 accesses non-volatile memory 920 over a high-speed bus 922. The non-volatile memory 920 is re-programmable and contains program data for the processor 910 including instrument communication protocols, synchronization information, a boot image, manufacturing history and diagnostic failure history.

The waveform generator 930 generates a synthesized waveform that a conventional pulse oximeter can process to calculate $SpO_2$ and pulse rate values or exception messages, as described above with respect to FIG. 4. However, in the present embodiment, as explained above, the waveform generator output does not reflect a physiological waveform. It is merely a waveform constructed to cause the external pulse oximeter to calculate the correct saturation and pulse rate. In an alternative embodiment, physiological data could be provided to the external pulse oximeter, but the external pulse oximeter would generally not be able to calculate the proper saturation values, and the upgrading feature would be lost. The waveform generator 930 is enabled if an interface cable 690 (FIG. 6), described below with respect to FIG. 10, with valid synchronization information is connected. Otherwise, the power to the waveform generator 930 is disabled.

The status indicators 982 are a set of LEDs on the front of the docking station 660 used to indicate various conditions including external power (AC), portable docked, portable battery charging, docking station battery charging and alarm. The serial data port 682 is used to interface with either a computer, a serial port of conventional pulse oximeters or serial printers via a standard RS-232 DB-9 connector 962. This port 682 can output trend memory, $SpO_2$ and pulse rate and support the system protocols of various manufacturers. The analog output 688 is used to interface with analog input chart recorders via a connector 964 and can output "real-time" or trend $SpO_2$ and pulse rate data. The nurse call output 684 from a connector 964 is activated when alarm limits are exceeded for a predetermined number of consecutive seconds. In another embodiment, data, including alarms, could be routed to any number of communications ports, and even over the Internet, to permit remote use of the upgrading pulse oximeter.

The PROM interface 940 accesses synchronization data 692 from the PROM 1010 (FIG. 10) in the interface cable 690 (FIGS. 6, 10) and provides synchronization status 942 to the docking station processor 910. The portable interface 970 provides the interconnection to the portable 610 (FIG. 6) through the docking station interface 760 (FIG. 7).

As shown in FIG. 9, external power 668 is provided to the docking station 660 through a standard AC connector 968 and on/off switch 969. When the docking station 660 has external power 668, the power supply 990 charges the battery in the portable power supply 730 (FIG. 7) and the battery, if any, in the docking station power supply 990. When the portable 610 (FIG. 6) is either removed or turned off, the docking station power 973 is removed and the docking station 660 is turned off, except for the battery charger portion of the power supply 990. The docking station power 973 and, hence, the docking station 660 turn on whenever a docked portable 610 (FIG. 6) is turned on. The portable 610 (FIG. 6) supplies power for an embodiment of the docking station 660 without a battery when external power 668 is removed or fails.

Figure 10:
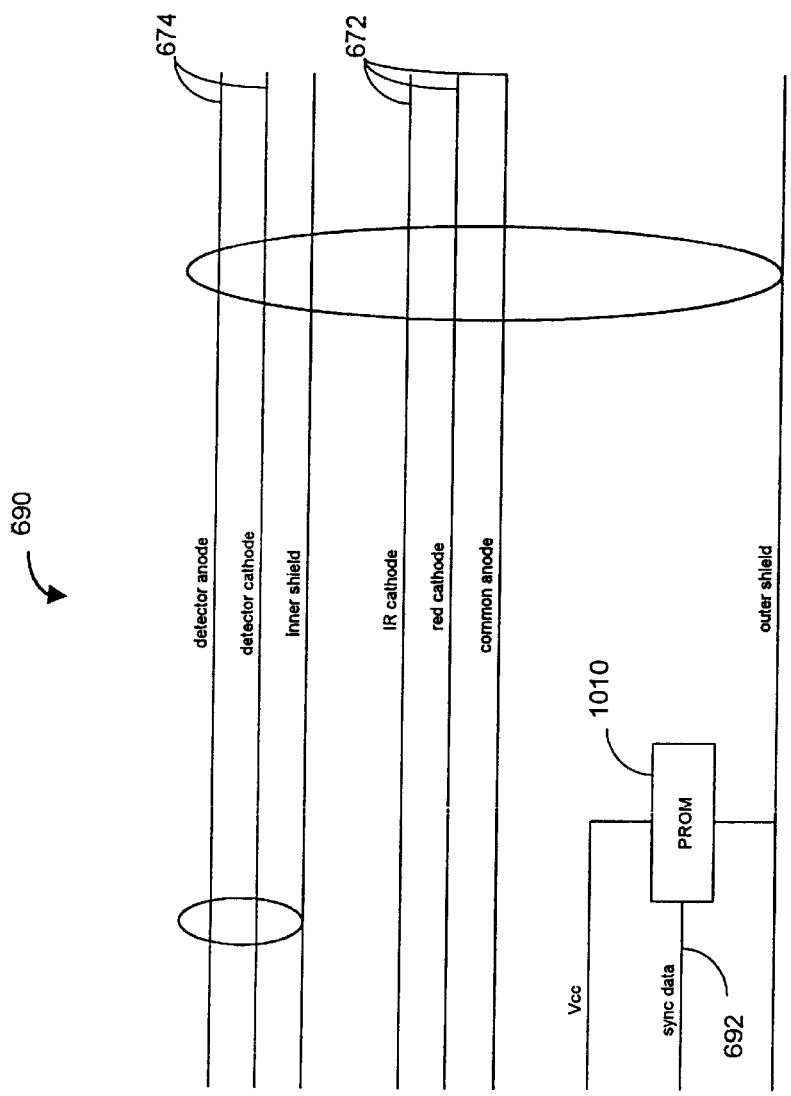
FIG. 10 is a schematic of the interface cable portion of FIG. 6.

FIG. 10 provides further detail regarding the interface cable 690 used to connect between the docking station 660 (FIG. 6) and the patient cable 230 (FIG. 2) of a host instrument 260 (FIG. 2). The interface cable 690 is configured to interface to a specific host instrument and to appear to the host instrument as a specific sensor. A PROM 1010 built into the interface cable 690 contains information identifying a sensor type, a specific host instrument, and the calibration curve of the specific host instrument. The PROM information can be read by the docking station 660 (FIG. 6) as synchronization data 692. Advantageously, the synchronization data 692 allows the docking station 660 (FIG. 6) to generate a waveform to the host instrument that causes the host instrument-to display $SpO_2$ values equivalent to those calculated by the portable 610 (FIG. 6). The interface cable 690 includes an LED drive path 672. In the embodiment shown in FIG. 10, the LED drive path 672 is configured for common anode LEDs and includes IR cathode, red cathode and common anode signals. The interface cable 690 also includes a detector drive path 674, including detector anode and detector cathode signals.

A menu option on the portable 610 (FIG. 6) also allows synchronization information to be calculated in the field. With manual synchronization, the docking station 660 (FIG. 6) generates a waveform to the host instrument 260 (FIG. 2) and displays an expected $SpO_2$ value. The user enters the $SpO_2$ value displayed on the host instrument using the portable keypad 750 (FIG. 7). These steps are repeated until a predetermined number of data points are entered and the $SpO_2$ values displayed by the portable and the host instrument are consistent.

Figure 11A:
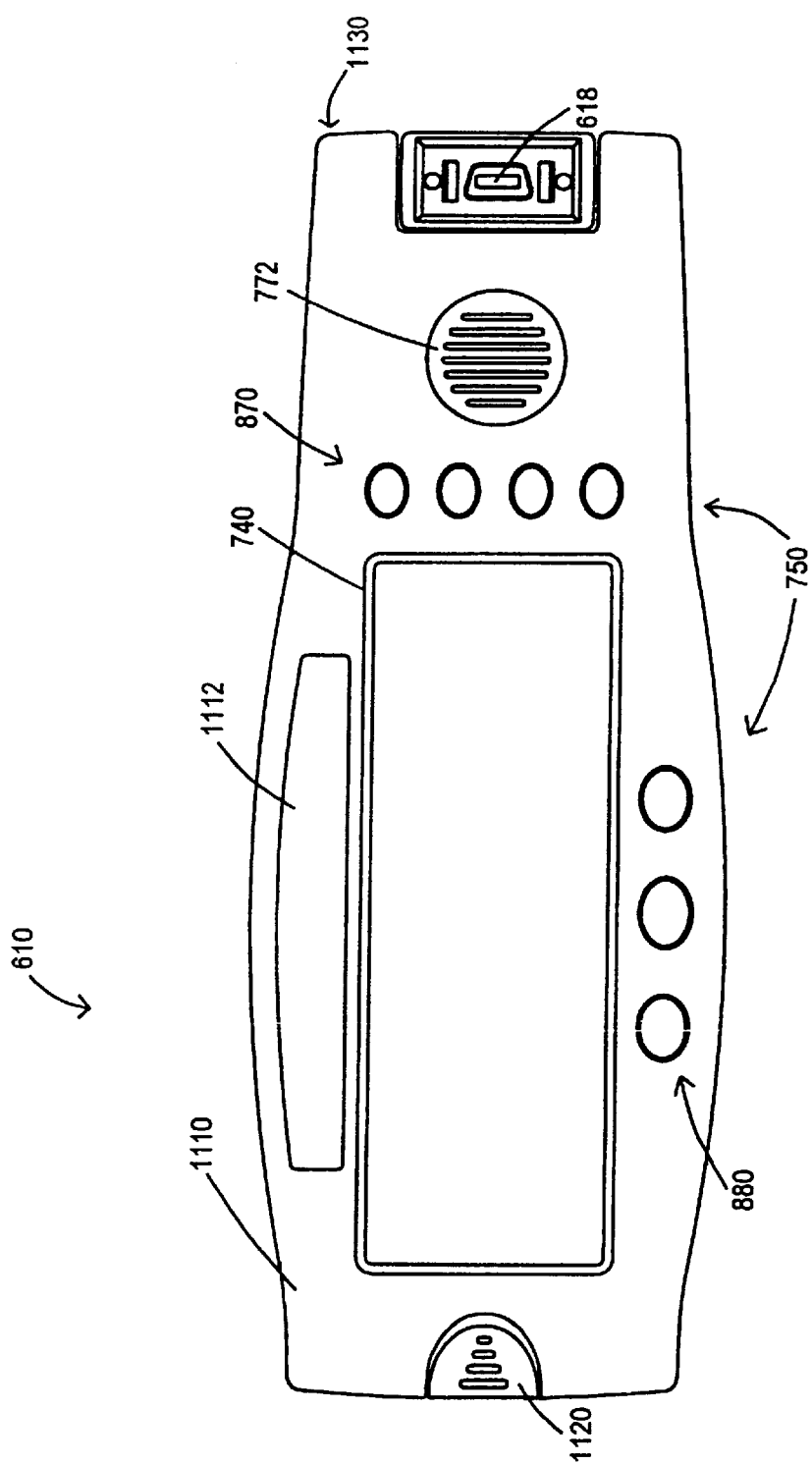
FIG. 11A is a front view of an embodiment of a portable pulse oximeter.
Figure 11B:
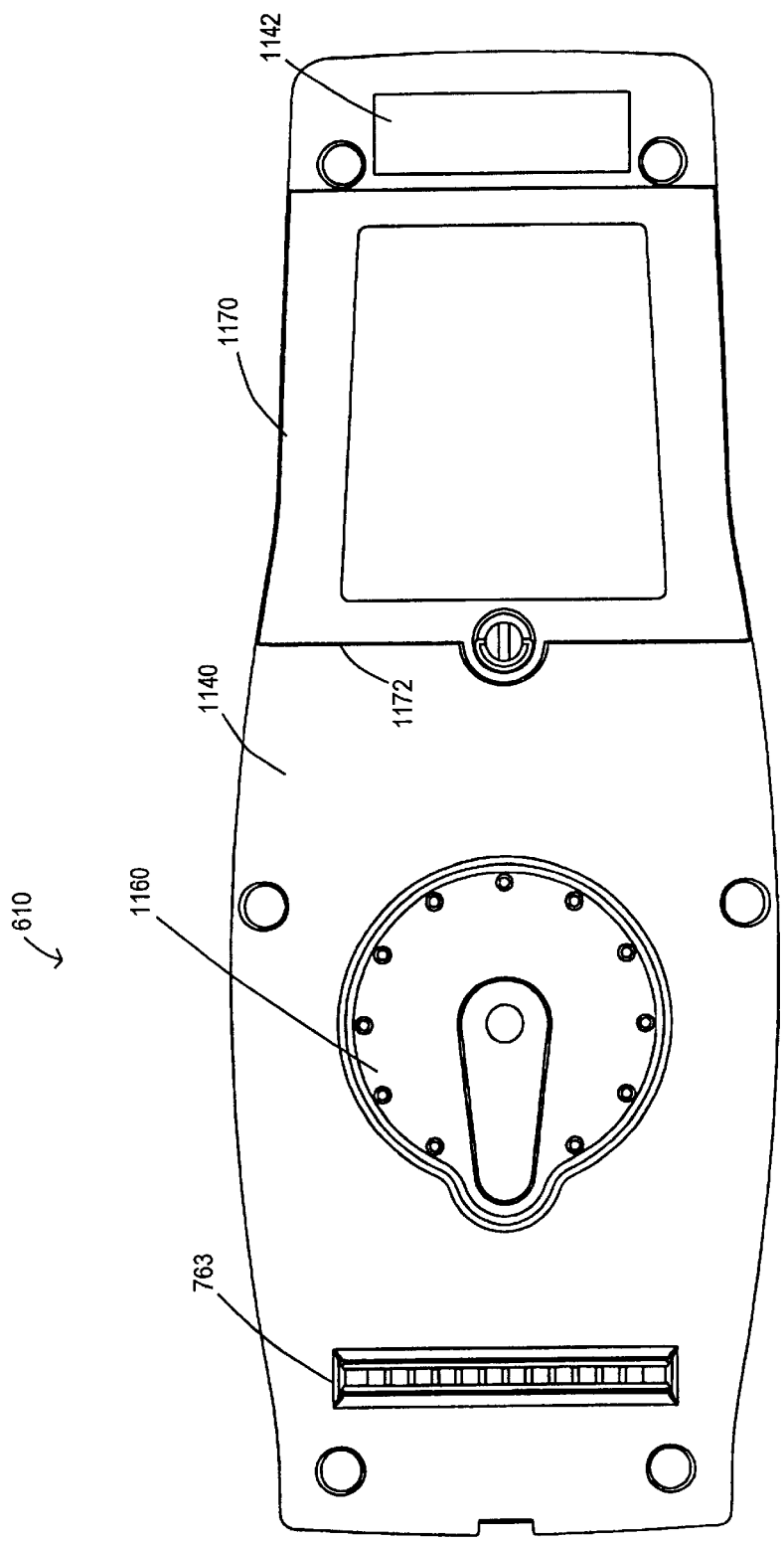
FIG. 11B is a back view of a portable pulse oximeter.
Figure 12A:
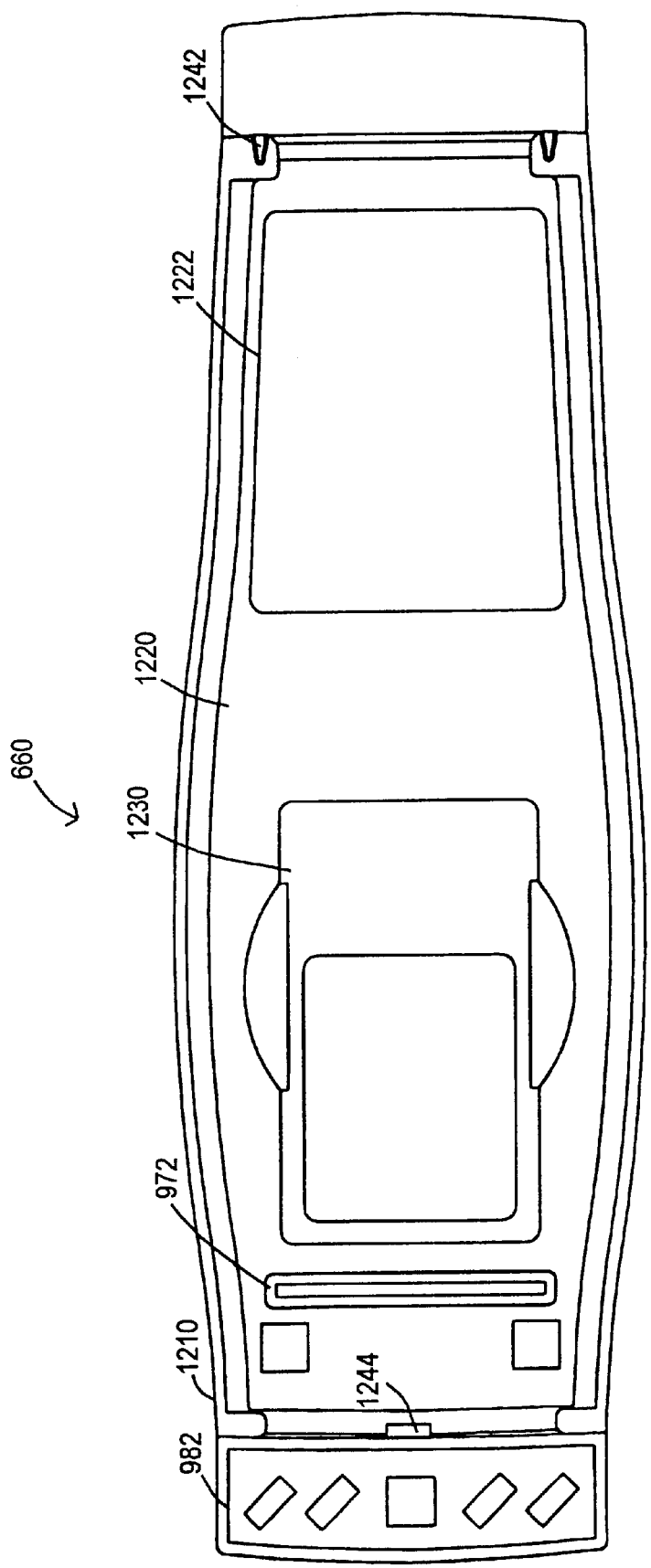
FIG. 12A is a front view of an embodiment of a docking station.
Figure 12B:
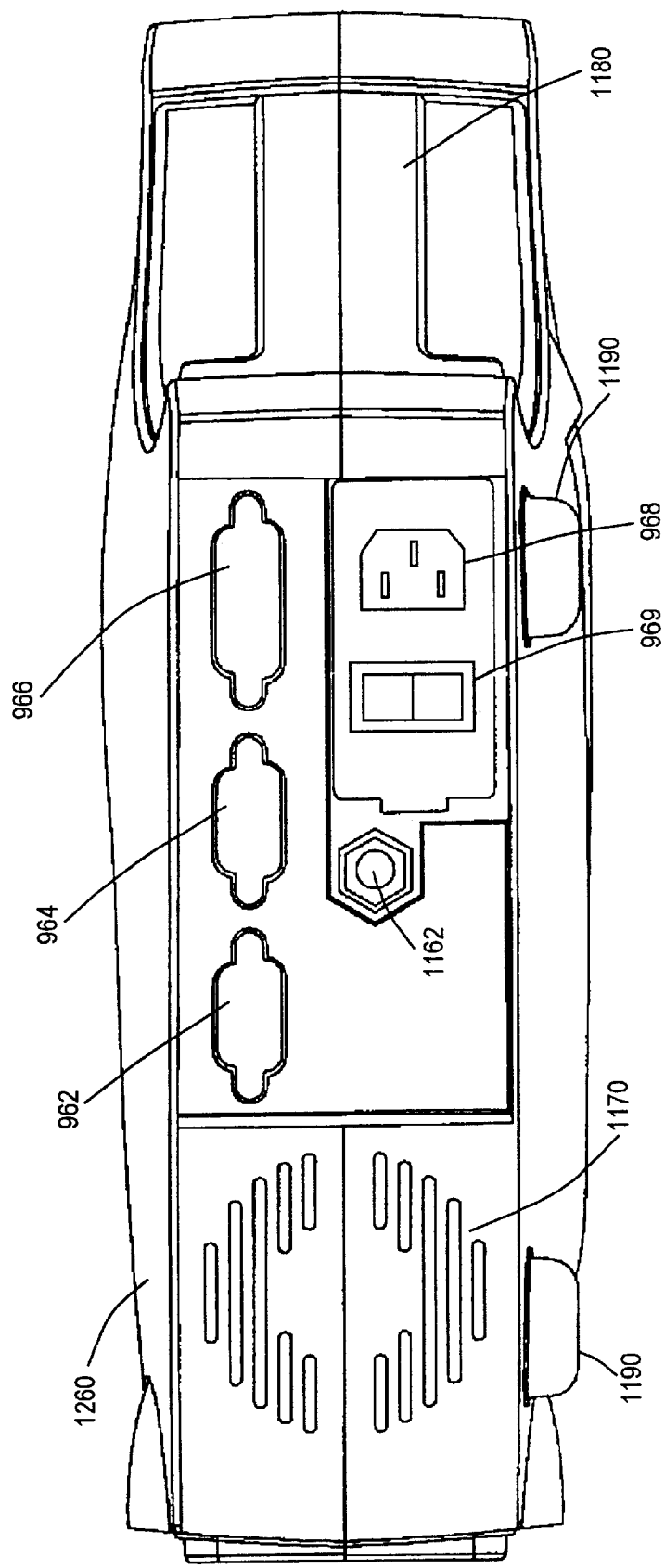
FIG. 12B is a back view of a docking station.
Figure 13:
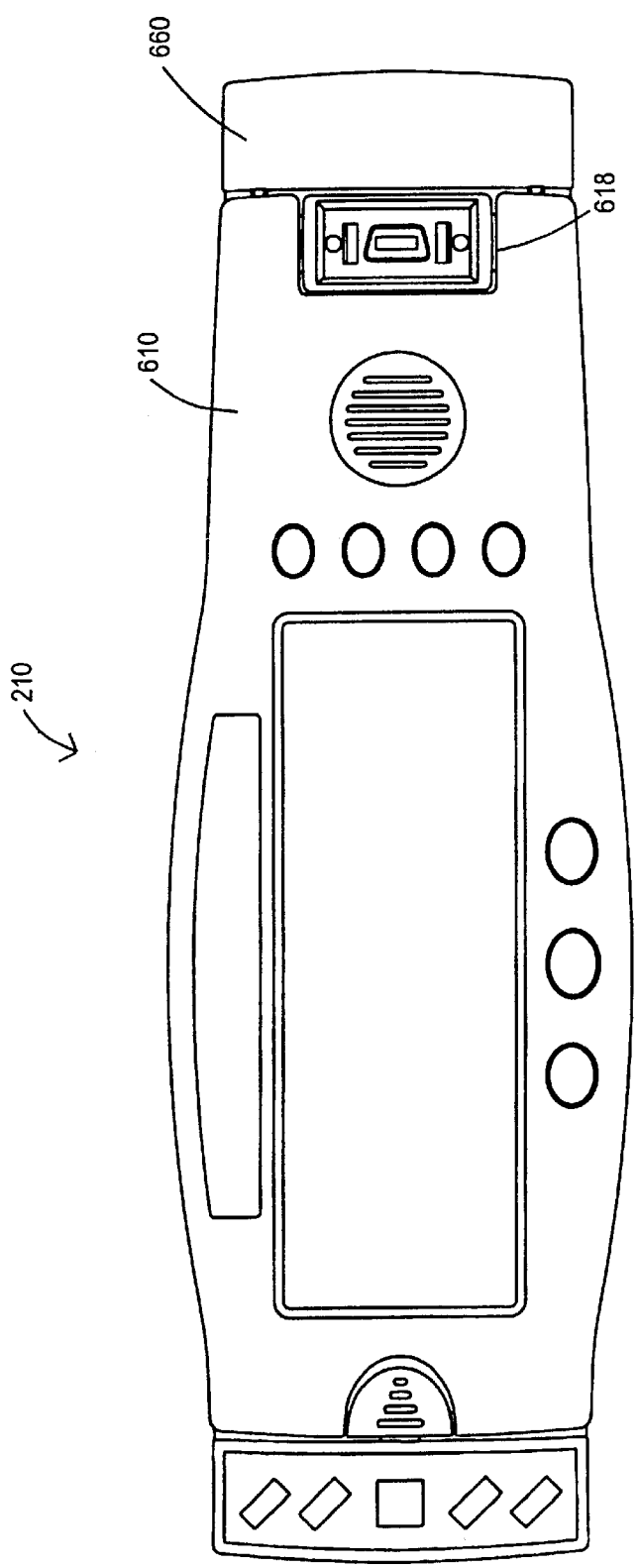
FIG. 13 is a front view of a portable docked to a docking station.

FIGS. 11A–B depict an embodiment of the portable 610, as described above with respect to FIG. 6. FIGS. 12A–B depict an embodiment of the docking station 660, as described above with respect to FIG. 6. FIG. 13 depicts an embodiment of the UPO 210 where the portable 610 is docked with the docking station 660, also as described above with respect to FIG. 6.

FIG. 11A depicts the portable front panel 1110. The portable 610 has a patient cable connector 618, as described above with respect to FIG. 6. Advantageously, the connector 618 is rotatably mounted so as to minimize stress on an attached patient cable (not shown). In one embodiment, the connector 618 can freely swivel between a plane parallel to the front panel 1110 and a plane parallel to the side panel 1130. In another embodiment, the connector 618 can swivel between, and be releasably retained in, three locked positions. A first locked position is as shown, where the connector is in a plane parallel to the front panel 1110. A second locked position is where the connector 618 is in a plane parallel to the side panel 1130. The connector 618 also has an intermediate locked position 45° between the first and the second locked positions. The connector 618 is placed in the first-locked position for attachment to the docking station 660.

Shown in FIG. 11A, the portable front panel 1110 also has a speaker 772, as described with respect to FIG. 7. Further, the front panel 1110 has a row of soft keys 870 and fixed keys 880, as described above with respect to FIG. 8. In addition, the front panel 1110 has a finger actuated latch 1120 that locks onto a corresponding catch 1244 (FIG. 12A) in the docking station 660, allowing the portable 610 to be releasably retained by the docking station 660. An OEM label can be affixed to a recessed area 1112 on the front panel 1110.

FIG. 11B depicts the portable back panel 1140. The back panel 1140 has a socket 763, a pole clamp mating surface 1160, and a battery pack compartment 1170. The socket 763 is configured to mate with a corresponding docking station plug 972 (FIG. 12A). The socket 763 and plug 972 (FIG. 12A) provide the electrical connection interface between the portable 610 and the docking station 660 (FIG. 12A). The socket 763 houses multiple spring contacts that compress against plated edge-connector portions of the docking station plug 972 (FIG. 12A). A conventional pole clamp (not shown) may be removably attached to the mating surface 1160. This conveniently allows the portable 610 to be held to various patient-side or bedside mounts for hands-free pulse oximetry monitoring. The portable power supply 730 (FIG. 7) is contained within the battery pack compartment 1170. The compartment 1170 has a removable cover 1172 for protection, insertion and removal of the portable battery pack. Product labels, such as a serial number identifying a particular portable, can be affixed with the back panel indent 1142.

FIG. 12A depicts the front side 1210 of the docking station 660. The front side 1210 has a docking compartment 1220, a pole clamp recess 1230, pivots 1242, a catch 1244, a plug connector 972 and LED status indicators 982. The docking compartment 1220 accepts and retains the portable 610 (FIGS. 11A–B), as shown in FIG. 13. When the portable 610 (FIGS. 11A–B) is docked in the compartment 1220, the pole clamp recess 1230 accommodates a pole clamp (not shown) attached to the portable's pole clamp mating surface 1160 (FIG. 11B), assuming the pole clamp is in its closed position. The portable 610 (FIGS. 11A–B) is retained in the compartment 1220 by pivots 1242 that fit into corresponding holes in the portable's side face 1130 and a catch 1244 that engages the portable's latch 1120 (FIG. 11A). Thus, the portable 610 (FIGS. 11A–B) is docked by first attaching it at one end to the pivots 1242, then rotating it about the pivots 1242 into the compartment 1220, where it is latched in place on the catch 1244. The portable 610 (FIGS. 11A–B) is undocked in reverse order, by first pressing the latch 1120 (FIG. 11A), which releases the portable from the catch 1244, rotating the portable 610 (FIGS. 11A–B) about the pivots 1242 out of the compartment 1220 and then removing it from the pivots 1242. As the portable is rotated into the compartment, the docking station plug 972 inserts into the portable socket 763 (FIG. 11B), providing the electrical interface between the portable 610 and the docking station 660. The status indicators 982 are as described above with respect to FIG. 9.

FIG. 12B depicts the back side 1260 of the docking station 660. The back side 1260 has a serial (RS-232 or USB) connector 962, an analog output and nurse call connector 964, an upgrade port connector 966, an AC power plug 968, an on/off switch 969 and a ground lug 1162. A handle 1180 is provided atone end and fan vents 1170 are provided at the opposite end. A pair of feet 1190 are visible near the back side 1260. A corresponding pair of feet (not visible) are located near the front side 1210 (FIG. 12A). The feet near the front side 1210 extend so as to tilt the front side 1210 (FIG. 12A) upward, making the display 740 (FIG. 13) of a docked portable 610 (FIG. 13) easier to read.

FIG. 13 illustrates both the portable 610 and the docking station 660. The portable 610 and docking station 660 constitute three distinct pulse oximetry instruments. First, the portable 610 by itself, as depicted in FIGS. 11A–B, is a handheld pulse oximeter applicable to various patient monitoring tasks requiring battery power or significant mobility, such as ambulance and ER situations. Second, the portable 610 docked in the docking station 660, as depicted in FIG. 13, is a standalone pulse oximeter applicable to a wide-range of typical patient monitoring situations from hospital room to the operating room. Third, the portable 610 docked and the upgrade port 966 (FIG. 12B) connected with an interface cable to the sensor port of a conventional pulse oximeter module 268 (FIG. 2) within a multiparameter patient monitoring instrument 260 (FIG. 2) or other conventional pulse oximeter, is a universal/upgrading pulse oximeter (UPO) instrument 210, as described herein. Thus, the portable 610 and docking station 660 configuration of the UPO 210 advantageously provides a three-in-one pulse oximetry instrument functionality.

Another embodiment of the docking station 660 incorporates an input port that connects to a blood pressure sensor and an output port that connects to the blood pressure sensor port of a multiparameter patient monitoring system (MPMS). The docking station 660 incorporates a signal processor that computes a blood pressure measurement based upon an input from the blood pressure sensor. The docking station 660 also incorporates a waveform generator connected to the output port that produces a synthesized waveform based upon the computed measurement. The waveform generator output is adjustable so that the blood pressure value displayed on the MPMS is equivalent to the computed blood pressure measurement. Further, when the portable 610 is docked in the docking station 660 and the blood pressure sensor is connected to the input port, the portable displays a blood pressure value according to the computed blood pressure measurement. Thus, in this embodiment, the docking station 660 provides universal/upgrading capability for both blood pressure and $SpO_2$.

Likewise, the docking station 660 can function as an universal/upgrading instrument for other vital sign measurements, such as respiratory rate, EKG or EEG. For this embodiment, the docking station 660 incorporates related sensor connectors and associated sensor signal processors and upgrade connectors to an MPMS or standalone instrument. In this manner, a variety of vital sign measurements can be incorporated into the docking station 660, either individually or in combination, with or without $SpO_2$ as a measurement parameter, and with or without the portable 610. In yet another embodiment, the docking station 660 can be configured as a simple $SpO_2$ upgrade box, incorporating a $SpO_2$ processor and patient cable connector for a $SpO_2$ sensor that functions with or without the portable 610.

Unlike a conventional standalone pulse oximeter, the standalone configuration shown in FIG. 13 has a rotatable display 740 that allows the instrument to be operated in either a vertical or horizontal orientation. A tilt sensor 950 (FIG. 9) indicates when the bottom face 1310 is placed along a horizontal surface or is otherwise horizontally-oriented. In this horizontal orientation, the display 740 appears in landscape mode (FIG. 8C). The tilt sensor 950 (FIG. 9) also indicates when the side face 1320 is placed along a horizontal surface or is otherwise horizontally oriented. In this vertical orientation, the display 740 appears in portrait mode (FIG. 8B). A soft key 870 on the portable 610 can override the tilt sensor, allowing the display to be presented at any 90° orientation, i.e. portrait, landscape, "upside-down" portrait or "upside-down" landscape orientations. The handheld configuration (FIG. 11A), can also present the display 740 at any 90° orientation using a soft key 870. In the particular embodiment described above, however, the portable 610 does not have a tilt sensor and, hence, relies on a soft key 870 to change the orientation of the display when not docked.

Figure 14:
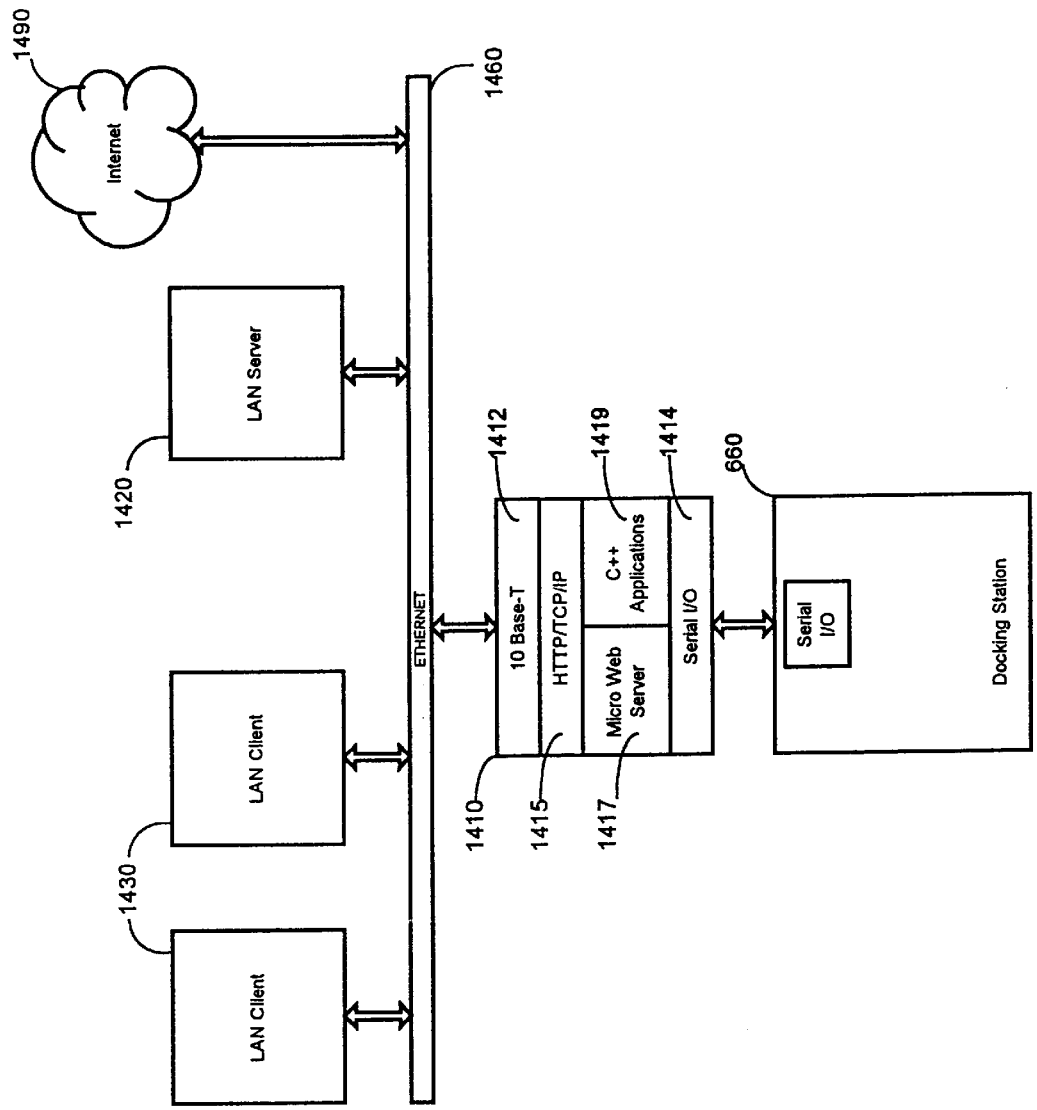
FIG. 14 is a block-diagram of one embodiment of a local area network interface for a docking station.

FIG. 14 illustrates the docking station 660 incorporated within a local area network (LAN). The LAN shown is Ethernet-based 1460, using a central LAN server 1420.to interconnect various LAN clients 1430 and other system resources such as printers and storage (not shown). An Ethernet controller module 1410 is incorporated with the docking station 660. The controller module 1410 can be incorporated within the docking station 660 housing or constructed as an external unit. In this manner, the UPO, according to the present invention, can communicate with other devices on the LAN or over the Internet 1490.

The Ethernet controller module 1410 can be embedded with web server firmware, such as the Hewlett-Packard (HP) BFOOT-10501. The module 1410 has both a 10 Base-T Ethernet interface for connection to the Ethernet 1460 and a serial interface, such as RS-232 or USB, for connection to the docking station 660. The module firmware incorporates HTTP and TCP/IP protocols for standard communications over the World Wide Web. The firmware also incorporates a micro web server that allows custom web pages to be served to remote clients over the Internet, for example. Custom C++ programming allows expanded capabilities such as data reduction, event detection and dynamic web page configuration.

As shown in FIG. 14, there are many applications for the docking station 660 to Ethernet interface. Multiple UPOs can be connected to a hospital's LAN, and a computer on the LAN could be utilized to upload pulse rate and saturation data from the various UPOs, displaying the results. Thus, this Ethernet interface could be used to implement a central pulse oximetry monitoring station within a hospital. Further, multiple UPOs from anywhere in the world can be monitored from a central location via the Internet. Each UPO is addressable as an individual web site and downloads web pages viewable on a standard browser, the web pages displaying oxygen saturation, pulse rate and related physiological measurements from the UPO. This feature allows a caregiver to monitor a patient regardless of where the patient or caregiver is located. For example a caregiver located at home in one city or at a particular hospital could download measurements from a patient located at home in a different city or at the same or a different hospital. Other applications include troubleshooting newly installed UPOs or uploading software patches or upgrades to UPOs via the Internet. In addition alarms could be forwarded to the URL of the clinician monitoring the patient.

The UPO may have other configurations besides the handheld unit described in connection with FIG. 5 or the portable 610 and docking station 660 combination described in connection with FIGS. 11–13. The UPO may be a module, with or without a display, that can be removably fastened to a patient via an arm strap, necklace or similar means. In a smaller embodiment, this UPO module may be integrated into a cable or connector used for attaching a sensor to a pulse oximeter. The UPO may also be a circuit card or module that can externally or internally plug into or mate with a standalone pulse oximeter or multiparameter patient monitoring system. Alternatively, the UPO may be configured as a simple standalone upgrade instrument.

Further, although a universal/upgrading apparatus and method have been mainly described in terms of a pulse oximetry measurement embodiment, the present invention is equally applicable to other physiological measurement parameters such as blood pressure, respiration rate, EEG and ECG, to name a few. In addition, a universal/upgrading instrument having a single physiological measurement parameter or a multiple measurement parameter capability and configured as a handheld, standalone, portable, docking station, module, plug-in, circuit card, to name a few, is also within the scope of the present invention.

The UPO has been disclosed in detail in connection with various embodiments of the present invention. These embodiments are disclosed by way of examples only and are not to limit the scope of the present invention, which is defined by the claims that follow. One of ordinary skill in the art will appreciate many variations and modifications within the scope of this invention.

What is claimed is:

1. A measurement apparatus comprising:
 a sensor having at least one emitter and an associated detector configured to attach to a tissue site, said detector providing a detector signal responsive to the intensity of energy from said emitter after it has passed through said tissue site;
 a first pulse oximeter in communication with said detector and configured to compute an oxygen saturation measurement based on said detector signal;
 a waveform generator responsive to said oxygen saturation measurement to generate at least one generated waveform based on said oxygen saturation measurement, wherein said at least one waveform is synthesized so that a second pulse oximeter receiving said waveform would calculate an oxygen saturation value generally equivalent to said oxygen saturation measurement.

2. The measurement apparatus of claim 1 wherein said at least one waveform comprises a first waveform and a second waveform, where the amplitude ratio of said first and second waveforms are selected so that said oxygen saturation value is generally equivalent to said oxygen saturation measurement.

3. The measurement apparatus of claim 2, wherein said first and second waveforms are generated from a look-up table.

4. The measurement apparatus of claim 3, wherein said first and second waveforms are triangular.

5. The measurement apparatus of claim 1, wherein said first pulse oximeter further computes a pulse rate measurement based on said detector signal, said generated waveform based in part on said pulse rate measurement in a manner such that said second pulse oximeter receiving said generated waveform would calculate a pulse rate value generally equivalent to said pulse rate measurement.

6. The measurement apparatus of claim 1 further comprising:

a portable portion comprising said first pulse oximeter; and a docking station portion comprising said waveform generator, wherein said portable portion is removably attached and in communication with said docking station portion when said portable portion is attached to said docking station portion.

7. The measurement apparatus of claim 6 further comprising:

a display mounted on said portable portion.

8. The measurement apparatus of claim 7, further comprising a tilt sensor, wherein the mode of said display is determined by the output of said tilt sensor.

9. The measurement apparatus of claim 8, wherein said tilt-sensor is provided by said docking station portion.

10. The measurement apparatus of claim 9, wherein an image on said display is oriented in response to said tilt sensor.

11. The measurement apparatus of claim 7, wherein an image on said display is rotatable in orientation with respect to said display in 90 degree increments.

12. A measurement apparatus comprising:

a first sensor port connectable to a sensor;

an upgrade port connectable to a second sensor port of an external measurement apparatus;

a signal processor that computes a measurement based on a signal input to said first sensor port;

a signal generator responsive to said measurement to produce a synthesized signal, said synthesized signal being provided to said upgrade port, wherein said synthesized signal is generated such that said external measurement apparatus will calculate a value generally equivalent to said measurement when said upgrade port is attached to said second sensor port.

13. The measurement apparatus of claim 12 wherein said sensor is generally incompatible with said second sensor port.

14. The measurement apparatus of claim 12 wherein said signal processor is an improved measurement apparatus from said external measurement apparatus.

15. The measurement apparatus of claim 12, wherein said measurement apparatus is a physiological monitor which calculates a physiological parameter, and wherein said external measurement apparatus is a physiological monitor which is capable of calculating said physiological parameter.

16. A measurement method comprising the steps of:

obtaining an intensity signal responsive to the oxygen content of blood at a tissue site;

computing an oxygen saturation measurement based on said intensity signal; and generating a waveform based on said oxygen saturation measurement, wherein said waveform is configured to cause a pulse oximeter receiving said waveform to calculate an oxygen saturation value generally equivalent to said oxygen saturation measurement.

17. The method of claim 16, further comprising providing said waveform to the sensor inputs of an pulse oximeter.

18. The measurement method of claim 17 wherein said generating step comprises:

reading waveform values from a waveform lookup table;

creating a first set of waveform data and a second set of waveform data based on said waveform values; and combining portions of said first set and said second set of waveform data into a set of modulated waveform data configured to be provided to said pulse oximeter.

19. The measurement method of claim 16 wherein said generating step further comprises:

inputting said oxygen saturation measurement to a calibration curve lookup table;

outputting a ratio from said calibration curve lookup table; and adjusting said second set of waveform data to correlate to said ratio.

20. The measurement method of claim 16 further comprising:

determining a pulse rate measurement based on said intensity signal; and adjusting the sample rate of said waveform so that said waveform is configured to cause said pulse oximeter receiving said waveform to display a pulse rate value generally equivalent to said pulse rate measurement.

21. A measurement method comprising the steps of:

sensing a physiological signal;

computing a physiological parameter based upon said signal;

synthesizing a waveform as a function of said physiological parameter, said synthesizing performed such that an external physiological monitor receiving said waveform will ascertain a value corresponding to said physiological parameter, further comprising outputting said waveform to a sensor input of said external physiological monitoring apparatus.

22. A measurement method comprising the steps of:

sensing a physiological signal;

computing a physiological parameter based upon said signal;

synthesizing a waveform as a function of said physiological parameter, said synthesizing performed such that an external physiological monitor receiving said waveform will ascertain a value corresponding to said physiological parameter, further comprising the steps of:

connecting an interface cable to said sensor input, said cable configured to transmit said waveform to said physiological monitoring apparatus and to provide a plurality of characterization data for said measurement apparatus; and reading said characterization data from said cable, said synthesizing step based on said data.

23. The measurement method of claim 22 wherein said physiological signal is an intensity signal responsive to the oxygen content of blood at a tissue site and said characterization data is a calibration curve relating a set of ratios to a set of oxygen saturation values.

24. A measurement apparatus comprising:

a first pulse oximeter configured to determine oxygen saturation measurements and pulse rate measurements based upon an intensity signal derived from a tissue site;

means for creating a waveform signal based upon said oxygen saturation measurement and said pulse rate measurements; and means for transmitting said waveform signal to a second pulse oximeter.

25. The measurement apparatus of claim 24 further comprising means for calibrating said waveform signal so that said second pulse oximeter displays oxygen saturation values generally equivalent to said oxygen saturation measurements.

26. The measurement apparatus of claim 24 further comprising means for timing said waveform signal so that said second pulse oximeter displays a pulse rate value generally equivalent to said pulse rate measurement.

27. The measurement apparatus of claim 24 further comprising means for displaying said oxygen saturation measurement and said pulse rate measurement on said first pulse oximeter.

28. The measurement apparatus of claim 27 further comprising means for sensing gravity and for altering an orientation mode of said means for displaying as a function of the orientation of said first pulse oximeter.

29. The measurement apparatus of claim 27 further comprising means for manually altering an orientation mode of said display means.

30. A measurement apparatus comprising:
   a portable portion having a sensor port, a processor, and a display, said sensor port configured to receive a signal indicative of a physiological parameter, said processor programmed to compute a physiological parameter measurement based upon said signal and to output said physiological parameter measurement to said display, said portable portion configured to operate as a handheld physiological monitor;
   a docking station configured to receive said portable portion and in communication with said portable portion; and
   wherein said portable portion has a docked position with said docking station in which the combination of said portable portion and said docking station has at least one function beyond that of said portable portion,
   wherein said at least one function comprises downloading a web page displaying said physiological parameter measurement when said docking station is addressed by a remote Internet client.

31. A measurement apparatus comprising:
   a portable portion having a sensor port, a processor, and a display, said sensor port configured to receive a signal indicative of a physiological parameter, said processor programmed to compute a physiological parameter measurement based upon said signal and to output said physiological parameter measurement to said display, said portable portion configured to operate as a handheld physiological monitor;
   a docking station configured to receive said portable portion and in communication with said portable portion; and
   wherein said portable portion has a docked position with said docking station in which the combination of said portable portion and said docking station has at least one function beyond that of said portable portion,
   wherein said portable portion has a key-actuated image rotatable display.

32. The measurement apparatus of claim 31 wherein said image rotatable display is a function of the orientation of said portable portion when said portable portion is in said docked position.

33. A measurement apparatus configured to function in both a first placement orientation and a second placement orientation, said apparatus comprising:
   a tilt sensor providing an output responsive to gravity; and
   a display having a first mode and a second mode, said display responsive to said tilt sensor to operate in a first mode when said apparatus is in said first placement orientation and in a second mode when said apparatus is in said second placement orientation, said first and second mode controlling the orientation of data on said display;
   wherein said measurement apparatus is a physiological monitor, said apparatus further comprising:
      a sensor port configured to receive a signal responsive to a physiological state; and
      a processor in communication with said sensor port and said tilt sensor output, said processor programmed to compute a physiological measurement based upon said signal and to determine whether said measurement apparatus is in said first placement orientation or said second placement orientation based upon said tilt sensor output, and to drive said display in said first mode or said second mode, and
      wherein said signal is a detected light intensity responsive to the attenuation at a tissue site and wherein said physiological measurement value is an oxygen saturation value.

34. A measurement apparatus configured to function in both a first placement orientation and a second placement orientation, said apparatus comprising:
   a tilt sensor providing an output responsive to gravity; and
   a display having a first mode and a second mode, sail display responsive to said tilt sensor to operate in a first mode when said apparatus is in said first placement orientation and in a second mode when said apparatus is in said second placement orientation, said first and second mode controlling the orientation of data on said display,
   further comprising a key that, when actuated, changes said display from said first mode to said second mode.

35. A measurement apparatus configured to function in both a first placement orientation and a second placement orientation, said apparatus comprising:
   a tilt sensor providing an output responsive to gravity; and
   a display having a first mode and a second mode, said display responsive to said tilt sensor to operate in a first mode when said apparatus is in said first placement orientation and in a second mode when said apparatus is in said second placement orientation, said first and second mode controlling the orientation of data on said display,
   wherein said measurement apparatus has a rectangular face with a shorter first edge and a longer second edge, said display forming at least a portion of said face, said second spatial orientation being with said first edge aligned generally horizontally and said second edge aligned generally vertically, said second mode providing a portrait presentation for said display.

36. A measurement method comprising the steps of:
   sensing a signal responsive to a physiological state;
   computing a physiological measurement based on said signal;
   determining the spatial orientation of a tilt sensor; and
   displaying said physiological measurement in a mode that is based upon said determining step,
   wherein said signal is an intensity signal responsive to attenuation at a tissue site and said physiological measurement is oxygen saturation.

37. A measurement method comprising the steps of:
   sensing a signal responsive to a physiological state;
   computing a physiological measurement based on said signal;
   determining the spatial orientation of a tilt sensor; and
   displaying said physiological measurement in a mode that is based upon said determining step,
   further comprising altering said mode upon the actuation of a key switch.

* * * * *

UNITED STATES PATENT AND TRADEMARK OFFICE
CERTIFICATE OF CORRECTION

PATENT NO. : 6,584,336 B1 Page 1 of 1
APPLICATION NO. : 09/516110
DATED : June 24, 2003
INVENTOR(S) : Ammar Ali et al.

It is certified that error appears in the above-identified patent and that said Letters Patent is hereby corrected as shown below:

In (75) Inventors, please change inventors' name, "Don Crothers" to --Don Carothers-- and "Julian Goldman" to --Julian M. Goldman--.

Signed and Sealed this

Twenty-fourth Day of October, 2006

JON W. DUDAS
*Director of the United States Patent and Trademark Office*